(12) United States Patent
Zhao

(10) Patent No.: US 12,276,633 B1
(45) Date of Patent: Apr. 15, 2025

(54) WOOD-DERIVED IONIC CONDUCTIVE CELLULOSE-Cu(II) FILM, THE PREPARATION METHOD THEREOF AND WOOD-DERIVED IONIC CONDUCTIVE CELLULOSE-Cu(II) SENSOR

(71) Applicant: Brian William Zhao, Scarsdale, NY (US)

(72) Inventor: Brian William Zhao, Scarsdale, NY (US)

(73) Assignee: Brian Zhao, Scarsdale, NY (US)

( * ) Notice: Subject to any disclaimer, the term of this patent is extended or adjusted under 35 U.S.C. 154(b) by 0 days.

(21) Appl. No.: 18/919,495

(22) Filed: Oct. 18, 2024

(51) Int. Cl.
*G01N 27/30* (2006.01)
*G01N 33/487* (2006.01)

(52) U.S. Cl.
CPC ....... *G01N 27/30* (2013.01); *G01N 33/48714* (2013.01)

(58) Field of Classification Search
None
See application file for complete search history.

(56) References Cited

U.S. PATENT DOCUMENTS

2021/0405042 A1 12/2021 Kim et al.

FOREIGN PATENT DOCUMENTS

| CN | 108982489 B | 12/2020 |
|----|-------------|---------|
| CN | 110591696 B | 6/2022  |

OTHER PUBLICATIONS

Microchemical Journal, 2022 107909 (Year: 2022).*
Solar Energy, 220, 852-863 (Year: 2021).*
Catalysis Letters, 152, 3558-3575 (Year: 2022).*

\* cited by examiner

*Primary Examiner* — Gurpreet Kaur
(74) *Attorney, Agent, or Firm* — NZ Carr Law Office

(57) ABSTRACT

The present invention provides a wood-derived ionic conductive cellulose-Cu(II) film and the preparation thereof as well as a wood-derived ionic conductive cellulose-Cu(II) sensor for sensing MPEA analogues. The wood-derived ionic conductive cellulose-Cu(II) film presents with excellent ion conductivity, high transmittance, and mechanical flexibility, transparent and flexible sensors capable of real-time detection of MPEA are demonstrated. More significantly, the wood-derived ionic conductive cellulose-Cu(II) sensor exhibits outstanding selectivity, ultralow theoretical detection limit, and excellent flexibility performance.

7 Claims, 31 Drawing Sheets

WOOD-DERIVED IONIC CONDUCTIVE CELLULOSE-Cu(II) FILM, THE PREPARATION METHOD THEREOF AND WOOD-DERIVED IONIC CONDUCTIVE CELLULOSE-Cu(II) SENSOR

FIELD

The present application relates to the ionic conductive technical field, more specifically relates to a wood-derived ionic conductive cellulose-Cu(II) film, the preparation method thereof and a wood-derived ionic conductive cellulose-Cu(II) sensor.

BACKGROUND

The illegal abuse of addictive drugs has currently become a global issue, posing enormous threats to human health. Specifically, ingesting even trace amounts of addictive drugs can cause irreversible damage to multiple vital organs. Hence, it is an urgent priority to developing sensitive, real-time, and cost-effective technologies for detecting trace amounts of addictive drugs. Methamphetamine is a typical addictive drug. However, due to restrictions on the availability of methamphetamine, N-methylphenethylamine (MPEA), an analog with a similar structure and chemical properties, is commonly regarded as a simulant for methamphetamine in detection analyses. Presently, conventional analytical methods for detecting MPEA frequently rely on advanced spectroscopic and biophysical technologies. Despite their advantages in sensitivity and accuracy, these technologies are normally hindered by high costs, bulky equipment, and complex tested film preparation, which limit their further applicability in rapid, real-time, and covert detection scenarios.

Chemical sensors have emerged as one type of promising practical equipment for detecting addictive drugs due to their portability and high sensitivity. Most of the currently developed chemical sensors interact with target analytes based on redox reactions or charge transfer/trapping, which rely on holes or electrons as charge carriers. Despite their wide detection range and good stability, these sensors commonly suffer from relatively low sensitivity, poor selectivity, and sometimes require high operating temperature. In contrast, chemical sensors based on ionic conductive materials demonstrate irreplaceable application potentials, including room-temperature operation capability, excellent selectivity, and high stability. Among this kind of sensors, active free ions play a key role as effective charge carriers. To further employ sensors in the field of addictive drug detection, it is crucial to consider the concealment of sensors, which is also a key aspect overlooked by most chemical sensors.

Therefore, the development of transparent and intelligent chemical sensors relied on novel ionic conductive materials can not only address the shortcomings of existing methods for detecting addictive drugs, but also meet the requirements of national security and public health, which demonstrate broad prospects in practical applications.

SUMMARY

Cellulose, as a key component of wood, is increasingly becoming a research focus in green electronics owing to its unique merits, such as natural abundance, mechanical flexibility, and biocompatibility. In previous studies, the inventor has found that nanofibrillated cellulose obtained from wood-derived cellulose, such as wood-derived ionic conductive cellulose (WICC) obtained via (2,2,6,6-tetramethylpiperidin-1-yl)-oxidanyl (TEMPO) treatment, exhibited both good transmittance and flexibility. Additionally, attributed to the introduction of sodium ions during the TEMPO treatment, WICC also demonstrated excellent ion conductivity. In this work, leveraging the merits of WICC, portable, transparent, and flexible sensors based on WICC as the ionic conductive material are developed for detecting trace amount of MPEA. Taking advantage of active metal ions as charge carriers, a small amount of copper ions ($Cu^{2+}$) are introduced into WICC (abbreviated as WICC-Cu(II)) to further enhance the sensitivity and selectivity of the WICC-based sensors.

In one aspect, the present disclosure provides a wood-derived ionic conductive cellulose-Cu(II) film (WICC-Cu(II) film), wherein the WICC-Cu(II) film has a transmittance over 87% despite the introduction of $Cu^{2+}$.

The WICC-Cu(II) film has a capacitance of over 4.5 nF when tested at a frequency of 50 Hz.

In one aspect, the present disclosure also provides a method of preparing the above WICC-Cu(II) film, including:

preparing softwood pulp suspension in a concentration of 0.08 g/mL, (2,2,6,6-tetramethylpiperidin-1-yl)-oxidanyl homogeneous solution in a concentration of 1 g/mL (TEMPO homogeneous solution), sodium bromide homogeneous solution in a concentration of 0.01 g/mL (NaBr homogeneous solution) and copper nitrate trihydrate solution in a concentration of 100 mM ($Cu(NO_3)_2$ solution);

mixing the NaBr homogeneous solution with the TEMPO homogeneous solution to prepare NaBr/TEMPO blended solution, then adding the NaBr/TEMPO blended solution and sodium hypochlorite solution (NaClO solution), into the softwood pulp suspension to prepare a blended suspension;

maintaining the blended suspension at pH 8.8-10.5 for 3-5 hours to obtain a purified cellulose suspension, following by washing and diluting the purified cellulose suspension, which is then dispersed into nanofiber to obtain nanocellulose suspension;

separating the nanofiber and the microfiber and collecting the supernatant to obtain a wood-derived ionic conductive cellulose homogeneous solution (WICC homogeneous solution);

evenly mixing the WICC homogeneous solution with the $Cu(NO_3)_2$ solution and deionized water and then drop-coating the obtained solution onto a substrate whose surface is treated with a plasma pretreatment and exposing the substrate at room temperature to cure the WICC-Cu(II) film for 10-13 hours, wherein the $Cu^{2+}$ concentration in the obtained solution is adjusted to about 0.5 mM.

In one aspect, the present disclosure also provides a wood-derived ionic conductive cellulose-Cu(II) sensor (WICC-Cu(II) sensor), for sensing N-methylphenethylamine, comprising:

a WICC-Cu(II) film as the sensing layer;

two transparent patterned electrodes as the cathode and the anode connecting the WICC-Cu(II) film; and a transparent substrate on which the WICC-Cu(II) film and the two transparent patterned electrodes are laid in sequence.

The lowest detection limit of the MPEA by the WICC-Cu(II) sensor is 0.02 μL (1.7 ppm).

The theoretical detection limit of the WICC-Cu(II) sensor is about 12 nL (1 ppm).

The WICC-Cu(II) sensor has an initial capacitance of 4.5-5.9 nF before exposed to MPEA when tested at a frequency of 50 Hz.

The WICC-Cu(II) sensor has a test capacitance of 0.54-0.63 nF after exposed to MPEA when tested at a frequency of 50 Hz.

The WICC-Cu(II) sensor has a short-term normalized response in a range about 7.3%-7.8% and a long-term normalized response in range about 7.4%-8.1% when exposed to 0.4 μL (34 ppm) of MPEA.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
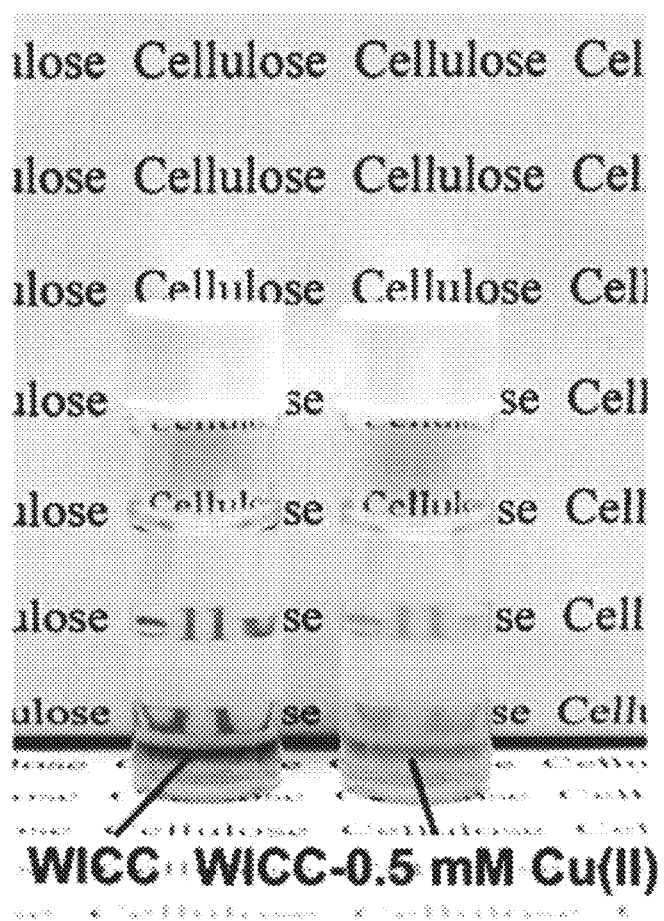
FIG. 1 shows the photo of the WICC solution and WICC-0.5 mM Cu(II) solution.

The present disclosure may be understood more readily by reference to the following detailed description of the preferred embodiments of the present disclosure and the Examples included herein. It is to be understood that the terminology used herein is provided for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents. The term "about" means a value falls within an accepted standard of error of the mean, when considered by one of ordinary skill in the art.

In order to clarify the advantages of the WICC-Cu(II) film prepared by the present disclosure over the conventional WICC film, the inventor tests the transmittance by a UV-vis spectrometer, the capacitance by a LCR meter and the impedance by an electrochemical station on the WICC-Cu (II) film prepared by the present disclosure and the conventional WICC film. Now the inventor briefly introduces the process for testing the transmittance, the capacitance and the impedance in detail.

(I) Test of Transmittance

At a temperature of 23° C.±2° C. and relative humidity of 50%±10%, the test is carried out on a UV-vis spectrometer (Agilent Technologies Co., Ltd., Cary 60) after no less than 50 hours of adjustment in accordance with GB/T2918-1989. The inventor turns on UV-vis spectrometer and preheats it for at least 20 minutes. Then the inventor places a standard plate, wherein the galvanometer is 100 scale and blocks the incident light and the galvanometer is 0. The inventor repeatedly adjusts 100 and 0 until stable, that is, T1 is 100. The inventor places the tested film while the luminous flux through the galvanometer is T2 on the scale. The inventor removes the standard plate and sets the trap, wherein the luminous flux measured on the galvanometer is the scattered luminous flux of the tested film and the instrument T4, followed by the inventor removes the tested film, wherein the luminous flux measured by the test galvanometer is the scattered luminous flux of the instrument T3. The inventor repeats the determination of 5 tested films and then calculates results. For each test film, the transmittance is expressed as a percentage. The transmittance is calculated by the following equation:

$$A = \frac{T_i}{T_t} \times 100\%$$

wherein the accurate to 0.1%, A is the transmittance, $T_i$ is the value of the total transmitted light flux through the tested film, and $T_r$ is the value of the incident light flux.

(II) Test of Capacitance

The inventor puts the WICC-Cu(II) film and the WICC film into the test fixture of a LCR meter (Tonghui TH2827C), adjusts the bridge to the capacitance measurement mode, selects the appropriate frequency and voltage, and reads the capacitance value displayed by the bridge.

It should be noted that when using LCR meter measurement, it is necessary to pay attention to whether the selected frequency and voltage meet the specifications of the WICC-Cu(II) film and the WICC film. The capacitance is calculated by the following equation:

$$C = K * \frac{L * W}{d}$$

wherein is the capacitance, L is the effective length of the tested film, W is the effective width, K is the equivalent constant, i.e. 39 pF/m, and d is the thickness of the tested film.

(III) Test of Impedance

The inventor puts the WICC-Cu(II) film and the WICC film into the appropriate size of the tested film, and cleans the surface to ensure the accuracy of the measurement results. Then the inventor selects the appropriate current and voltage range, and sets the electrochemical station (Biologic SAS, VMP-3) to the required mode. The inventor uses the four-wire method to connect the probe to ensure good contact between the probe and the tested film surface. The inventor starts the electrochemical station and records the current and voltage values. The resistance value of the film is calculated according to Ohm's law. The inventor then analyzes the measurement results and calculates the average resistance value and standard difference of the film. The impedance is calculated by the following equation:

$$R = \frac{\rho}{d} * \frac{L}{W}$$

wherein is the impedance of the tested film, ρ is the electrical impedance of the tested film, L is the length of the tested film, W is the width of the tested film, and d is the thickness of the tested film.

The inventor divides the WICC-Cu(II) film into 15 mm×15 mm tablets respectively in a total number of 6, wherein when the tablet has a thickness less than 0.1 mm, an accuracy is required at least 0.001 mm and when the table has a thickness bigger than 0.1 mm, an accuracy is required at least 0.01 mm. The overall data are summarized in Table 1, and an average value calculated for the WICC-Cu(II) film is shown in Table 2.

TABLE 1

Summaries of Values of Transmittance and Capacitance of Tested WICC-Cu(II) Film

| Tested film | WICC-Cu(II) film | Type of tests |
|---|---|---|
| No.1 | 87% | Transmittance |
|  | 4.57 nF | Capacitance |
| No.2 | 90% | Transmittance |
|  | 5.10 nF | Capacitance |

TABLE 1-continued

Summaries of Values of Transmittance and Capacitance of Tested WICC-Cu(II) Film

| Tested film | WICC-Cu(II) film | Type of tests |
|---|---|---|
| No.3 | 88% | Transmittance |
|  | 4.52 nF | Capacitance |
| No.4 | 89% | Transmittance |
|  | 4.83 nF | Capacitance |
| No.5 | 86% | Transmittance |
|  | 4.92 nF | Capacitance |
| No.6 | 88% | Transmittance |
|  | 4.78 nF | Capacitance |

TABLE 2

Average Values of Tested WICC-Cu(II) Film

| Transmittance | Capacitance |
|---|---|
| 88% | 4.79 nF |

Seen from the above tables, it can be concluded that due to the introduction of $Cu^{2+}$, the WICC-Cu(II) film prepared by the present disclosure is a sensitive material maintained high transmittance of over 87% in the visible light range, a high capacitance of over 4.79 nF when tested at a frequency of 50 Hz. The threshold values of the above two values in Table 2 come from the lowest values presented in Table 1.

The visual comparison of transmittance between the conventional WICC solution and the WICC-Cu(II) solution prepared in the present disclosure is made to further clarify the advantage of the WICC-Cu(II) film. The two solutions are respectively put into a 5 mL glass medicine bottles with a written paper as the background. To provide the best contrast, the inventor chooses a WICC solution with a concentration of 0.5 mM $Cu^{2+}$ (abbreviated as WICC-0.5 mM Cu(II) solution). Seen from FIG. 1, compared to the pure WICC solution without copper ions, the transmittance of the WICC-0.5 mM Cu(II) solution exhibited almost no decrease. It can be concluded that, despite the introduction of $Cu^{2+}$, WICC-Cu(II) solution prepared in the present disclosure still has good transmittance. Despite the introduction of $Cu^{2+}$, a film formed from the WICC-Cu(II) solution has good transmittance, such as having a transmittance of over 87% in the visible light range.

Figure 2:
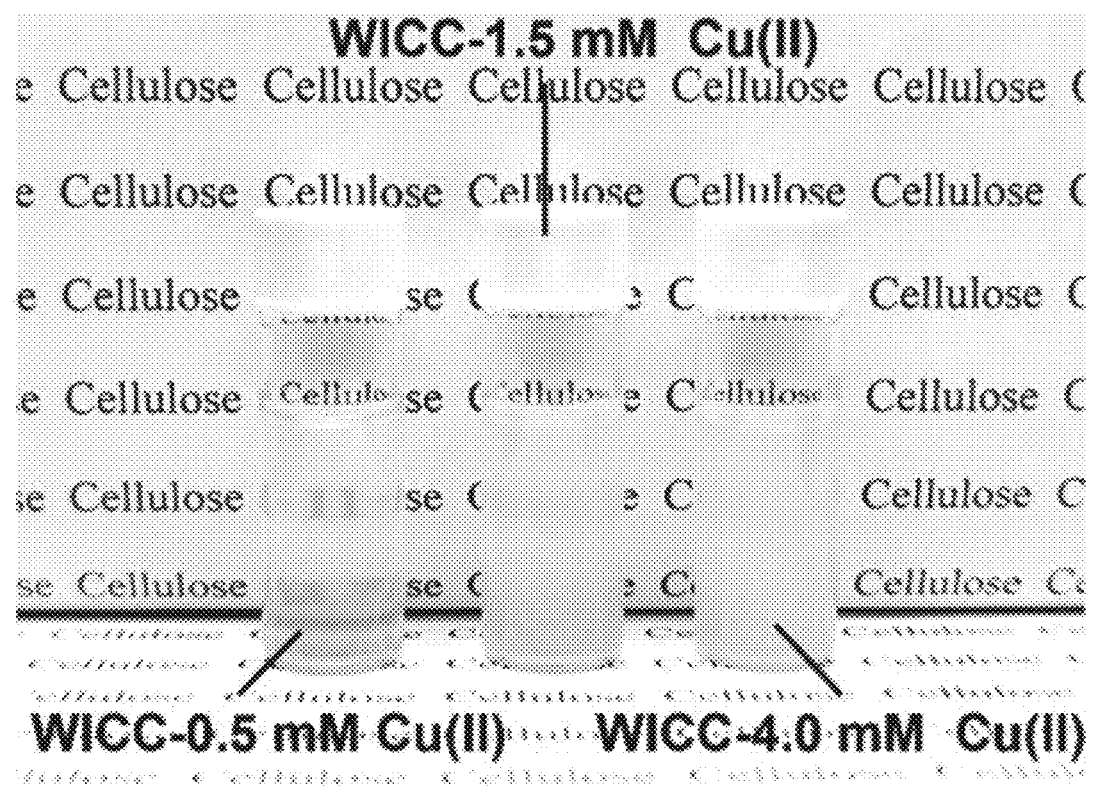
FIG. 2 shows the photo of the WICC-0.5 mM Cu(II) solution, WICC-1.5 mM Cu(II) solution, and WICC-4.0 mM Cu(II) solution.

Now the inventor wants to explore the influence of different $Cu^{2+}$ concentrations on the transmittance of the WICC-Cu(II) solution to balance ion conductivity and transmittance of the WICC-Cu(II) film. Seen from FIG. 2, further increasing the concentration of $Cu^{2+}$ in the WICC solution resulted in a notable decrease in transmittance, which might be attributed to the aggregation or precipitation of WICC induced by excessive divalent metal ions.

Figure 3:
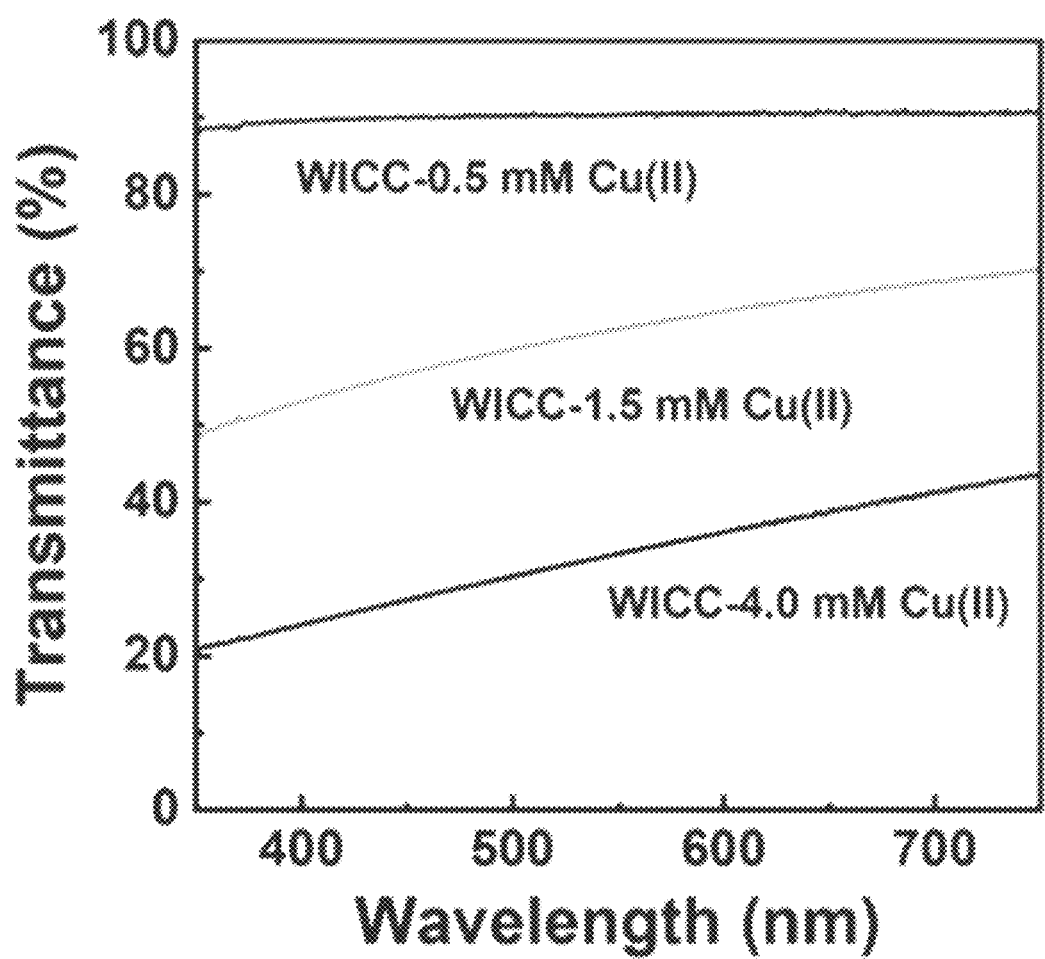
FIG. 3 shows the transmittance of the WICC-Cu(II) films with different $Cu^{2+}$ concentrations.

After the above exploration, the inventor tests and investigates the comparison of the transmittance of the WICC-Cu(II) films with different $Cu^{2+}$ concentrations with the test method of transmittance as set forth. The inventor prepares WICC-Cu(II) films with a $Cu^{2+}$ concentration of 0.5 mM, 1.5 mM and 4.0 mM and tests their transparencies. The results show that, with the increase of $Cu^{2+}$ concentration in the WICC, the transmittance of the WICC-Cu(II) film obviously decreases, As depicted in FIG. 3, the WICC-0.5 mM Cu(II) film showed a high transmittance (over 87%) in the visible range and the transmittance is almost stable in different wavelengths. In contrast, WICC-1.5 mM Cu(II) film and WICC-4.0 mM Cu(II) film respectively show an increase of transmittance with the increase of wavelength, but their transparencies are all below 63% and 41%, respectively.

Thus, considering the invisible requirement of the transparent conductive cellulose in practical applications, the present disclosure provides a method for preparing WICC-0.5 mM Cu(II), i.e. a concentration of 0.5 mM $Cu^{2+}$ in the WICC solution is targeted during the preparation process. The preparation method of the above WICC-Cu(II) film will be described in detail.

One of the steps for preparation of the WICC-Cu(II) film includes a reaction where the softwood pulp suspension is processed by TEMPO solution, whose mechanism is shown as follows:

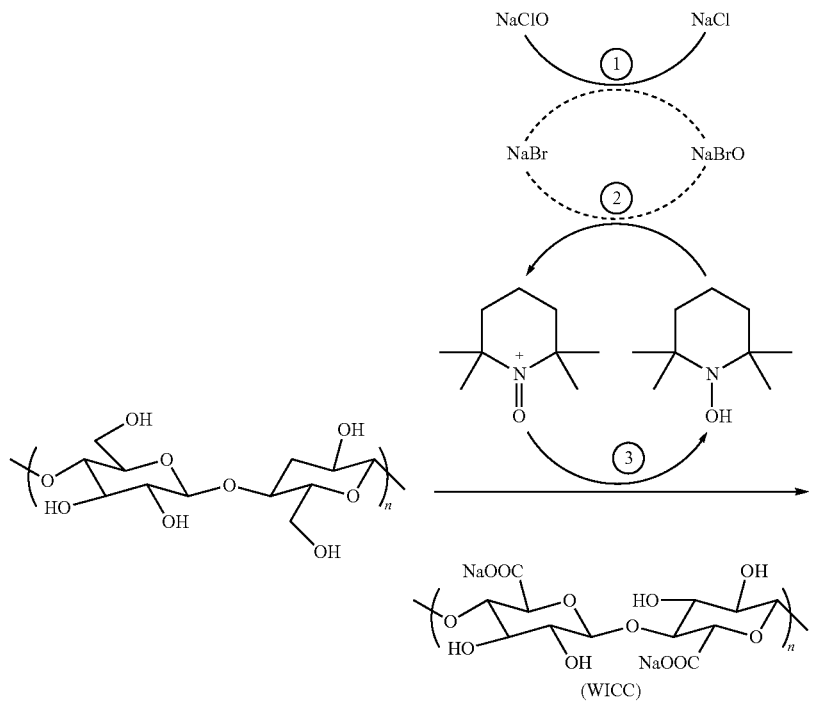

The reaction principle of TEMPO treatment on WICC can be explained as follows. The NaBr/TEMPO blended solution sustains a table solution due to the fact that no conditions of redox reaction exist until the addition of NaClO solution.

① The NaClO solution has strong oxidation function on NaBr solution, which converts NaBr to NaBrO.

② NaBrO reacts with TEMPOH 1. TEMPO 2 gains a proton and an electron to be reduced to TEMPOH 1, and can also lose an electron to be oxidized to TEMPOHA 3 (See mechanism below). Under acidic conditions, TEMPO 2 exists in a protonated state. After proton coupling and electron transfer, peroxy radical is removed, peroxy acid is generated, and then the activity is restored. Under neutral conditions, peroxy free radicals are converted to peroxy acid through alkoxamine generation and β-hydrogen atom transfer, and then the antioxidant activity is restored through carbon center free radical dissociation and TEMPO 2 regeneration.

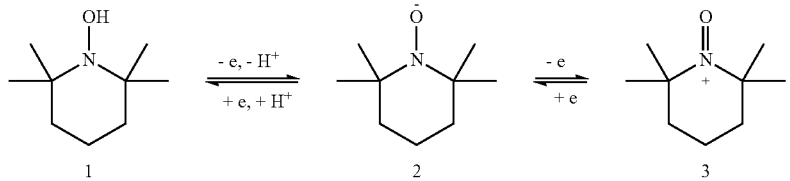

③ untreated WICC reacts with TEMPOHA 3 and is oxidized to form the TEMPO treated WICC solution needed in the present disclosure.

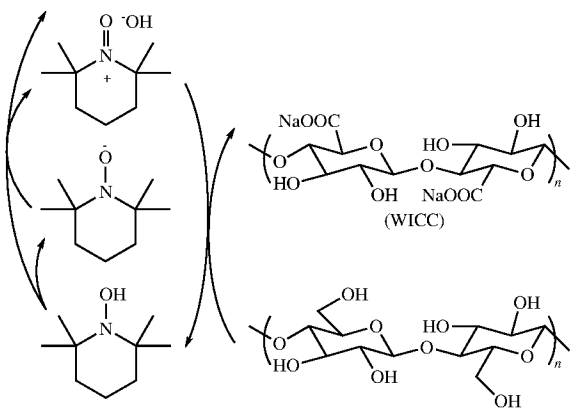

Things to note about this reaction are:

First, NaHCO₃ is usually added to adjust the reaction pH between 8.6 and 9.5, while the pH of 7.5% NaClO on the market is 12.7 (when the pH is greater than 12, the stability of NaClO is better). According to the reaction mechanism, the reason for the reaction system to control pH is to ensure the stability of hypochlorite and hypobromate. If pH is too high, such as greater than about 9.5, excessive oxidation will occur and the ethanol will be oxidized to acid; if pH is too low, such as less than about 8.6, the stability of hypochlorite and hypobromate cannot be guaranteed.

Second, adding potassium bromide or sodium bromide as a cocatalyst, its effect is to generate hypobromate, which is because hypobromate is easier to react with TEMPOH 1 than hypochlorite;

Third, for primary alcohols, the solvent is often dichloromethane with less polarity. Because the greater the polarity of the solvent, the more unfavorable the formation of TEMPO 2 ions, that is, the more unfavorable the reaction.

Further, the method in the present disclosure includes preparing the WICC-0.5 mM Cu(II) film, which is achieved by firstly measuring and then adjusting the $Cu^{2+}$ concentration in the WICC-Cu(II) solution. The measurement of $Cu^{2+}$ concentration can be realized by methods including but not limited to the spectrophotometry. When the $Cu^{2+}$ concentration in the prepared WICC-Cu(II) solution is measured to be far from 0.5 mM, the $Cu^{2+}$ concentration can be increased by adding $Cu(NO_3)_2$ solution and the $Cu^{2+}$ concentration can be decreased by NaOH solution for precipitation, both the processes are accompanied by the adjustment of proper pH. Below the measurement of the $Cu^{2+}$ concentration is by Neocuproin-Hydrochlorid spectrophotometry. In other words, in some embodiments, a copper-containing solution, such as $Cu(NO_3)_2$ solution may be added to the TEMPO treated WICC solution to introduce $Cu^{2+}$ in the TEMPO treated WICC solution (i.e., WICC-Cu(II) solution). The concentration of the $Cu^{2+}$ in the WICC-Cu(II) solution may be increased by adding a copper-containing solution, such as $Cu(NO_3)_2$ solution, into the WICC-Cu(II) solution. The concentration of the $Cu^{2+}$ in the WICC-Cu(II) solution may be decreased by adding a hydroxyl-containing solution, such as NaOH solution, into the WICC-Cu(II) solution. The pH of the WICC-Cu(II) solution may be monitored and adjusted during the addition of the copper-containing solution (and the hydroxyl-containing solution when needed). In some embodiments, if the pH of the WICC-Cu(II) solution is too high, $HNO_3$ solution is added to reduce the pH of the WICC-Cu(II) solution. If the pH of the WICC-Cu(II) solution is too low, acetic acid is added to increase the pH of the WICC-Cu(II) solution. The pH of the WICC-Cu(II) solution may be maintained in a range between about 8.6 and about 9.5.

The instrument used in the present disclosure is 722 spectrophotometer; 50 mm cuvette; 25 mL plug cues. Reagents include: 1) Copper standard stock solution in a concentration 1 mg/mL; 2) Copper standard solution in a concentration of 5 μg/mL of copper; 3) 10% (m/v) hydroxylamine hydrochloride solution; 4) 0.2% (m/v) Neocuprol Solution; 5) 37.5% (m/v) sodium citrate solution; 6) Acetate-sodium acetate buffer with a pH of about 5.7.

In some embodiments, the prepared WICC-Cu(II) solution is pretreated in order to form a WICC-Cu(II) film. The pretreatment of the prepared WICC-Cu(II) solution is performed by drawing and placing 50 mL prepared WICC-Cu (II) solution in a 150 ml beaker, adding 5 mL of nitric acid to form a mixed solution, heating and digesting the mixed solution on an electric hot plate and evaporated to about 10 mL, then cooling the mixed solution and adding 5 mL Nitric acid and 1 mL perchloric acid to the cooled mixed solution, continuing to heat and digest, steam until nearly dry, adding 40 mL of water, heating and boiling for 3 min, and then cooling again, transferring the resulting solution to a 50 mL volumetric flask and diluting it with water to the marking line (if there is precipitation, it should be filtered to remove).

Then it comes to the drawing of standard curves, which is performed by drawing of standard curves by accurately absorbing 0.00 mL, 0.50 mL, 1.00 mL, 2.00 mL, 3.00 mL, 5.00 mL of the quasi-solution of 5.00 μg/mL copper standard, adding water to 15.0 mL of $Cu(NO_3)_2$ solution in a 25 mL colorimetric tube, adding 1.5 mL of hydroxylamine hydrochloride solution, 3 mL of sodium citrate solution, 3 mL of acetic acid-sodium acetate buffer, and 1.5 mL of neocupalin solution, mixing the above solution in the colorimetric tube, adding water to the marking tube, evenly mixing the solution, and stewing for 5 minutes, then taking the reagent blank as the reference, measuring the absorbance at 457 nm with a 50 mm cuvette, and repeating each experimental point for 3 times, adopting the copper concentration as the abscissa, wherein the average absorbance A is used as the ordinate, and then drawing the standard curve, then calculating the linear range in the curve. The regression equation is $$y=k*x+b$$

wherein, the correlation coefficient r is chosen as 0.9985, and the molar absorbance coefficient ε is chosen as $1.0\times10^4$ L/mol·cm. The determination of $Cu^{2+}$ concentration is performed by absorbing 15 mL of the prepared WICC-Cu(II) solution into a 25 mL colorimetric tube, which is followed by the operation of a standard curve experiment. Calculation formula is as follows:

$$c = \frac{A - A_0 - a}{bV}$$

Wherein c is the $Cu^{2+}$ concentration (μg/mL), A is the absorbance value of the sample/distilled water; $A_0$ is the absorbance value of reagent blank/distilled water; a is the intercept of the regression equation; b is the slope of the regression equation; V is the sample volume (mL).

Copper nitrate trihydrate ($Cu(NO_3)_2 \cdot 3H_2O$), sodium hypochlorite (NaClO) solution, (2,2,6,6-tetramethylpiperidin-1-yl)-oxidanyl (TEMPO) used in the present disclosure are purchased from Adamas, Aladdin, and Sigma-Aldrich, respectively. In addition, specific to the present application, concentrations of the above solutions are pre-determined to prepare WICC-0.5 mM Cu(II), that is, softwood pulp suspension in a concentration of 0.08 g/mL, (2,2,6,6-tetramethylpiperidin-1-yl)-oxidanyl homogeneous solution in a concentration of 1 g/mL, i.e. TEMPO homogeneous solution, sodium bromide homogeneous solution in a concentration of 0.01 g/mL, i.e. NaBr homogeneous solution and copper nitrate trihydrate solution in a concentration of 100 mM, i.e. $Cu(NO_3)_2$ solution.

Preparation Example 1

2.0 g softwood pulp is gradually added in 25 mL deionized water and suspended through vigorous agitation to obtain the softwood pulp suspension. 40 mg TEMPO is dissolved in 40 mL of deionized water with ultrasonication for 40 minutes to obtain the TEMPO homogeneous solution. 0.2 g of sodium bromide (NaBr) is dissolved in 20 mL of deionized water to obtain the NaBr homogeneous solution, and 24.2 g $Cu(NO_3)_2 \cdot 3H_2O$ powders are dissolved in 800 mL deionized water to prepare metal ions solutions to obtain $Cu(NO_3)_2$ solution.

Mixing the 20 mL NaBr homogeneous solution with the 40 mL TEMPO homogeneous solution to prepare NaBr/TEMPO blended solution, then adding the NaBr/TEMPO blended solution and 50 mL sodium hypochlorite solution, i.e. NaClO solution, into the softwood pulp suspension to form a blended suspension, after which its pH will be adjusted.

Next, an alkali, such as 0.5 M sodium hydroxide, is added to the blended suspension, and the pH of the blended suspension is maintained at 9.5~10 for 3.5~4 hours to obtain a purified cellulose suspension. Then, the purified cellulose suspension is washed and diluted, which is then dispersed into nanofiber, followed by diluting with deionized water and scattering into nanofibers in a crusher to obtain nanocellulose suspension.

The nanofibers and the microfibers are then separated, and the supernatant is collected, i.e., separating nanofibers from the microfibers after the high-speed centrifugation at 9000~9500 rpm for 30~40 minutes and collecting the supernatant to obtain a wood-derived ionic conductive cellulose homogeneous solution, i.e. WICC homogeneous solution.

The WICC-Cu(II) films with different $Cu^{2+}$ concentrations could be obtained by blending varying amounts of $Cu(NO_3)_2$ solution with the WICC homogeneous solution. In some embodiments, evenly mixing the 0.25 g WICC homogeneous solution with the $Cu(NO_3)_2$ solution and deionized water, i.e. mixing 0.25 g of WICC suspension, $Cu(NO_3)_2$ solution (0 μL, 10 μL, 30 μL, and 80 μL) in batches respectively with deionized water (1.75 mL, 1.74 mL, 1.71 mL, and 1.67 mL) together, and then stirring the mixed solutions for 2~3 hours to obtain a uniform solution. 12~15 mL NaOH solution is added to the WICC homogeneous solution with $Cu(NO_3)_2$ solution to decrease the concentration of $Cu^{2+}$ from 0.60 mM to 0.49 mM. In some embodiments, the $Cu^{2+}$ ions in the solution are not chemically reacting with the molecules of the WICC homogeneous solution and are existing in the uniform solution as free ions. Next, the uniform solution is drop-coated onto a substrate, wherein the substrates are treated with a plasma pretreatment for 6~8 minutes to enhance hydrophilicity, adhesion and to remove surface impurities. Next, the substrates coated with the uniform solution are exposed at room temperature for 10~12 hours to cure the WICC-0.49 mM Cu(II) solution and obtain the WICC-0.49 mM Cu(II) film. The above experiment is repeated 10 times to obtain 10 pieces of WICC-0.49 mM Cu(II) films, whose experimental conditions and properties are measured to take the averages value for characterization comparison later on.

Preparation Example 2

4.0 g softwood pulp is gradually added in 50 mL deionized water and suspended through vigorous agitation to obtain the softwood pulp suspension. 60 mg TEMPO is dissolved in 60 mL of deionized water with ultrasonication for 75 minutes to obtain the TEMPO homogeneous solution. 0.4 g of sodium bromide (NaBr) is dissolved in 40 mL of deionized water to obtain the NaBr homogeneous solution, and 24.2 g $Cu(NO_3)_2 \cdot 3H_2O$ powders are dissolved in 1200 mL deionized water to prepare metal ions solutions to obtain $Cu(NO_3)_2$ solution.

Mixing the 40 mL NaBr homogeneous solution with the 60 mL TEMPO homogeneous solution to prepare NaBr/TEMPO blended solution, then adding the NaBr/TEMPO blended solution and 150 mL sodium hypochlorite solution, i.e. NaClO solution, into the softwood pulp suspension to form a blended suspension, after which its pH will be adjusted. The blended suspension may be the TEMPO treated WICC solution described above.

Next, an alkali, such as 0.7 M sodium hydroxide, is added to the blended suspension and the pH of the blended suspension is maintained at pH 9.5~10.5 for 4~5 hours to obtain a purified cellulose suspension. The purified cellulose suspension is washed and diluted, which is then dispersed into nanofiber, followed by diluting with deionized water and scattering into nanofibers in a crusher to obtain nanocellulose suspension.

The nanofibers and the microfibers are then separated, and the supernatant is collected, i.e. separating nanofibers from the microfibers after the high-speed centrifugation at 8000~8500 rpm for 50~60 minutes and collecting the supernatant to obtain a wood-derived ionic conductive cellulose homogeneous solution, i.e. WICC homogeneous solution.

The WICC-Cu(II) films with different $Cu^{2+}$ concentrations could be obtained by blending varying amounts of $Cu(NO_3)_2$ solution with the WICC homogeneous solution. In some embodiments, evenly mixing the 0.5 g WICC homogeneous solution with the $Cu(NO_3)_2$ solution and deionized water, i.e. mixing 0.5 g of WICC suspension, $Cu(NO_3)_2$ solution (0 μL, 20 μL, 60 μL, and 160 μL) in batches respectively with deionized water (3.50 mL, 3.48 mL, 3.42 mL, and 3.34 mL) together, and then stirring the mixed solutions for 3.5~4 hours to obtain a uniform solution. 49~52 mL $Cu(NO_3)_2$ solution is added to the WICC homogeneous solution with $Cu(NO_3)_2$ solution to increase the concentration of $Cu^{2+}$ from 0.40 mM to 0.51 mM. In some embodiments, the $Cu^{2+}$ ions in the solution are not chemically reacting with the molecules of the WICC homogeneous solution and are existing in the uniform solution as free ions. Next, the uniform solutions is drop-coated onto a substrate, wherein the substrates are treated with a plasma pretreatment for 10~14 minutes to enhance hydrophilicity, adhesion and remove surface impurities. Next, the substrates coated with the uniform solution are exposed at the substrate at room temperature for 12~14 hours to cure the WICC-0.51 mM Cu(II) solution to obtain the WICC-0.51 mM Cu(II) film. The above experiment is repeated 10 times to obtain 10 pieces of WICC-0.51 mM Cu(II) films, whose experimental conditions and properties are measured to take the averages value for characterization comparison later on.

Preparation Example 3

6.0 g softwood pulp is gradually added in 75 mL deionized water and suspended through vigorous agitation to obtain the softwood pulp suspension. 80 mg TEMPO is dissolved in 80 mL of deionized water with ultrasonication for 70 minutes to obtain the TEMPO homogeneous solution. 0.6 g of sodium bromide (NaBr) is dissolved in 60 mL of deionized water to obtain the NaBr homogeneous solution, and 24.2 g $Cu(NO_3)_2 \cdot 3H_2O$ powders are dissolved in 1000 mL deionized water to prepare metal ions solutions to obtain $Cu(NO_3)_2$ solution.

Mixing the 60 mL NaBr homogeneous solution with the 40 mL TEMPO homogeneous solution to prepare NaBr/TEMPO blended solution, then adding the NaBr/TEMPO blended solution and 90 mL sodium hypochlorite solution, i.e. NaClO solution, into the softwood pulp suspension to form a blended suspension, after which its pH will be adjusted. The blended suspension may be the TEMPO treated WICC solution described above.

Next, an alkali, such as 0.6 M sodium hydroxide, is added to the blended suspension, and the pH of the blended suspension is maintained at 10~10.5 for 4.5~ 5 hours to obtain a purified cellulose suspension. Then, the purified cellulose suspension is washed and diluted, which is then dispersed into nanofiber, followed by diluting with deionized water and scattering into nanofibers in a crusher to obtain nanocellulose suspension.

The nanofibers and the microfibers are then separated, and the supernatant is collected, i.e. separating nanofibers from the microfibers after the high-speed centrifugation at 7500~8000 rpm for 90~100 minutes and collecting the supernatant to obtain a wood-derived ionic conductive cellulose homogeneous solution, i.e. WICC homogeneous solution.

The WICC-Cu(II) films with different $Cu^{2+}$ concentrations could be obtained by blending varying amounts of $Cu(NO_3)_2$ solution with the WICC homogeneous solution. In some embodiments, evenly mixing the 0.75 g WICC homogeneous solution with the $Cu(NO_3)_2$ solution and deionized water, i.e. mixing 0.75 g of WICC suspension, $Cu(NO_3)_2$ solution (0 μL, 30 μL, 90 μL, and 240 μL) in batches respectively with deionized water (5.25 mL, 5.22 mL, 5.13 mL, and 5.01 mL) together, and then stirring the mixed solutions for 2~3 hours to obtain a uniform solution. 27~30 mL NaOH solution is added to the WICC homogeneous solution with $Cu(NO_3)_2$ solution to decrease the concentration of $Cu^{2+}$ from 0.55 mM to 0.50 mM. In some embodiments, the $Cu^{2+}$ ions in the solution are not chemically reacting with the molecules of the WICC homogeneous solution and are existing in the uniform solution as free ions. Next, the uniform solutions is drop-coated onto a substrate, which has been treated with a plasma pretreatment for 7~9 minutes to enhance hydrophilicity, adhesion and to remove surface impurities. Next, the substrates with the uniform solutions coated thereon are exposed at room temperature for 11~13 hours to cure the WICC-0.50 mM Cu(II) solution and obtain the WICC-Cu(II) film. The above experiment is repeated 10 times to obtain 10 pieces of WICC-0.50 mM Cu(II) films, whose experimental conditions and properties are measured to take the averages value for characterization comparison later on.

The inventor respectively tests the prepared WICC-Cu(II) films in the above preparation examples and results are shown in Table 3. Data in the Table 3 is collected from average values from experimental conditions and properties of WICC-Cu(II) films in each preparation examples.

TABLE 3

Transmittance, Capacitance and Impedance of Prepared WICC-Cu(II) Films

|  | Preparation Example 1 WICC- 0.49 mM Cu(II) | Preparation Example 2 WICC- 0.51 mM Cu(II) | Preparation Example 3 WICC- 0.50 mM Cu(II) |
|---|---|---|---|
| pH of WICC treated with TEMPO | 9.8 | 10.3 | 10.1 |
| Period maintained for the pH/hour | 3.8 | 4.8 | 4.3 |
| Plasma pretreatment time/min | 7 | 13 | 8 |
| Period for curing the film/hour | 11 | 13.5 | 12 |
| Transmittance | 86.8% | 87.3% | 88% |
| Capacitance/nF | 4.8 | 4.4 | 4.5 |

Seen from the table, it can be concluded that a pH around 10.1 of WICC treated with TEMPO, a period around 4.3 hours maintained for the pH, a plasma pretreatment time of the substrate around 8 minutes and a period around 12 hours for curing the film is best preparation condition for transmittance; a pH around 9.8 of WICC treated with TEMPO, a period around 3.8 hours maintained for the pH, a plasma pretreatment time around 7 minutes and a period around 11 hours for curing the film is the best preparation condition for capacitance.

Now the inventor selects the WICC-0.50 mM Cu(II) film presenting a better comprehensive properties to perform the following characterizations. The following tested WICC-Cu(II) films all refer to WICC-0.50 mM Cu(II) films if not otherwise indicated.

Figure 4:
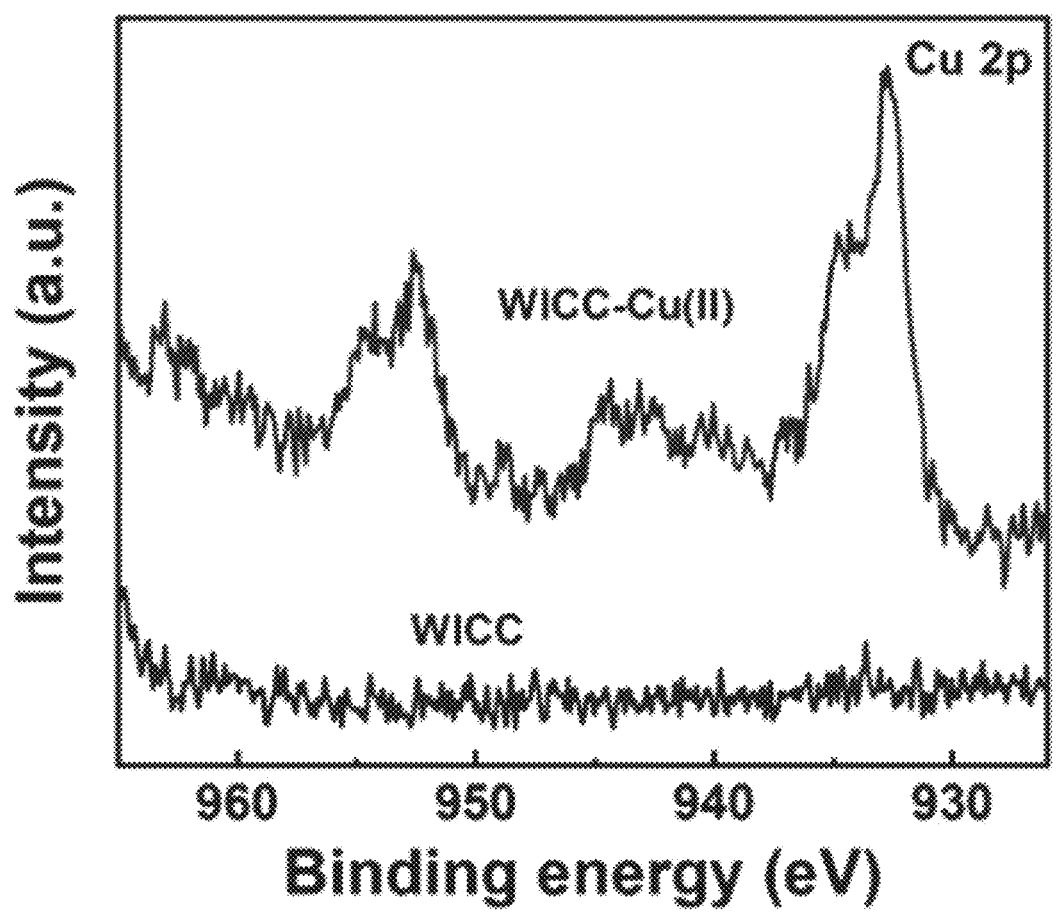
FIG. 4 shows the Cu 2p spectra of the WICC film and WICC-Cu(II) film.

To validate the successful introduction of $Cu^{2+}$ into WICC, X-ray photoelectron spectroscopy (XPS) is employed. As depicted in FIG. 4, the Cu 2p spectrum of the WICC-0.50 mM Cu(II) film exhibited new characteristic peaks compared with those of the WICC film.

Figure 5:
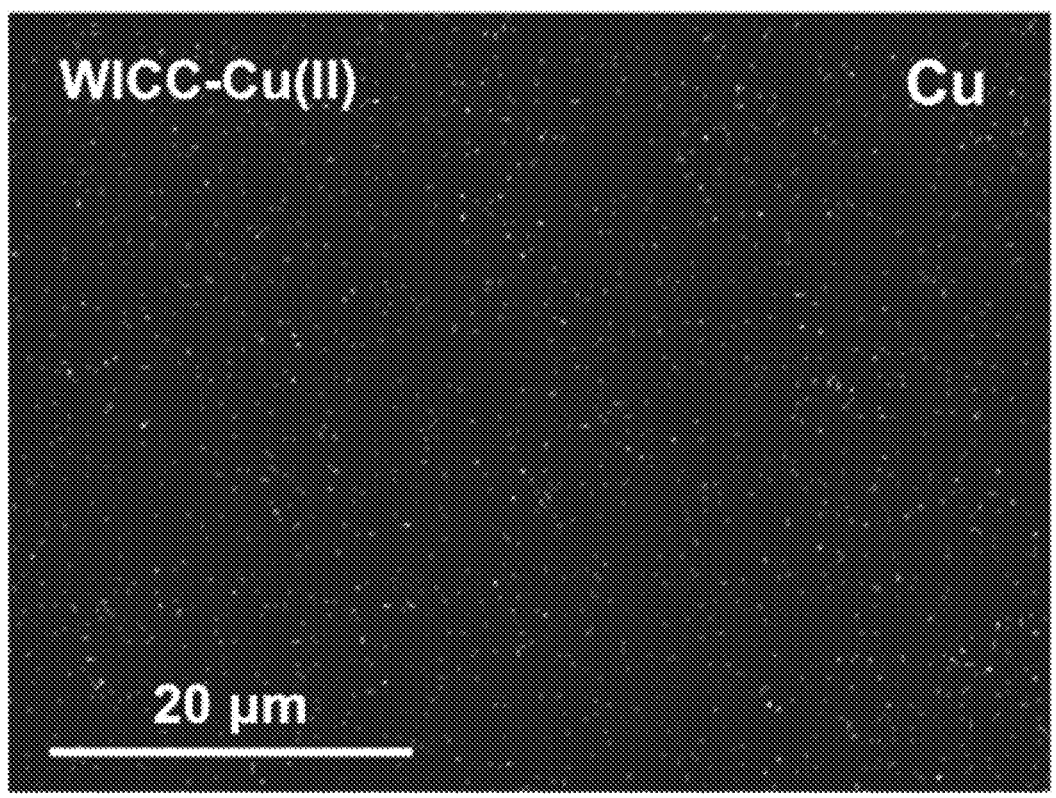
FIG. 5 shows the distribution of Cu element in the WICC-Cu(II) film obtained from EDS analysis.
Figure 6:
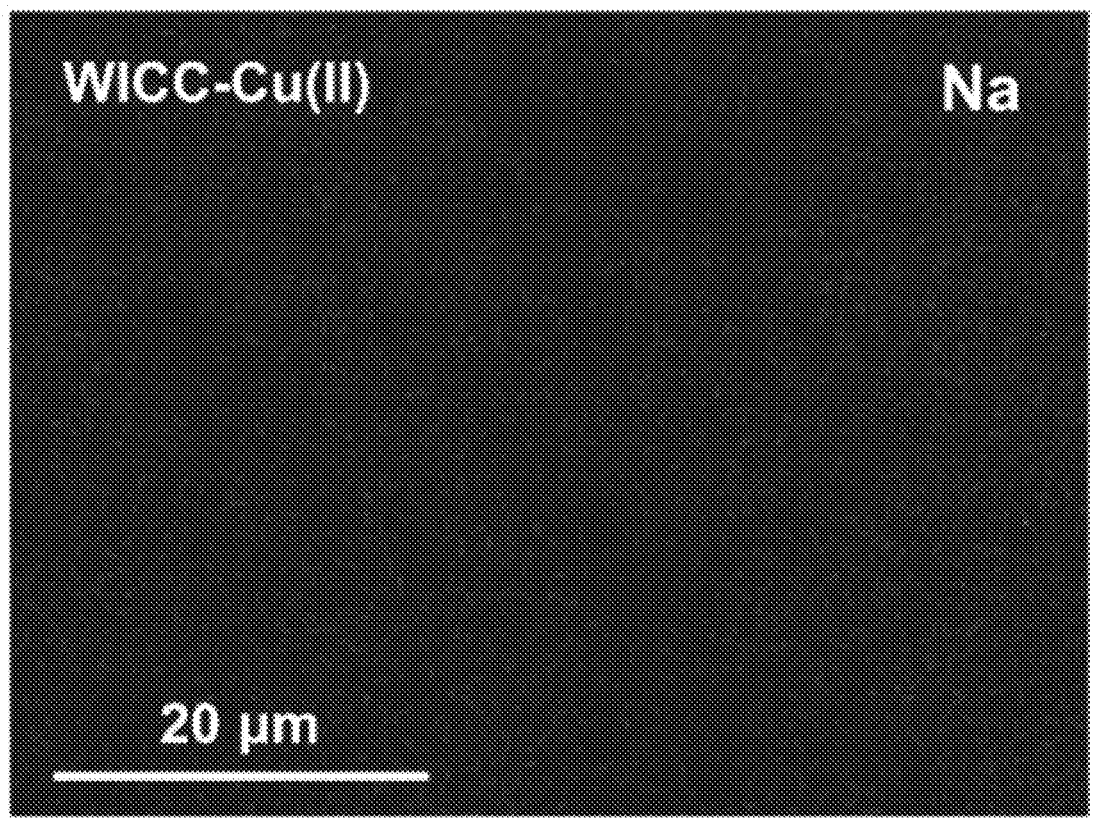
FIG. 6 shows the distribution of Na element in the WICC-Cu(II) film obtained from EDS analysis.

Besides, energy dispersive spectroscopy (EDS) is also utilized to validate the homogeneous distribution of $Cu^{2+}$ within the WICC-0.50 mM Cu(II) film. As depicted in FIG. 5, Cu element is uniformly dispersed in the film, proving the preparation of the WICC-0.50 mM Cu(II) sensing layer. In addition, the uniform distribution of Na element is also observed in the WICC-0.50 mM Cu(II) film, as depicted in FIG. 6. As described above, $Cu^{2+}$ functions as charge carriers to improve sensitivity and selectivity of a sensing layer made from the WICC-0.50 mM Cu(II) film.

Figure 7:
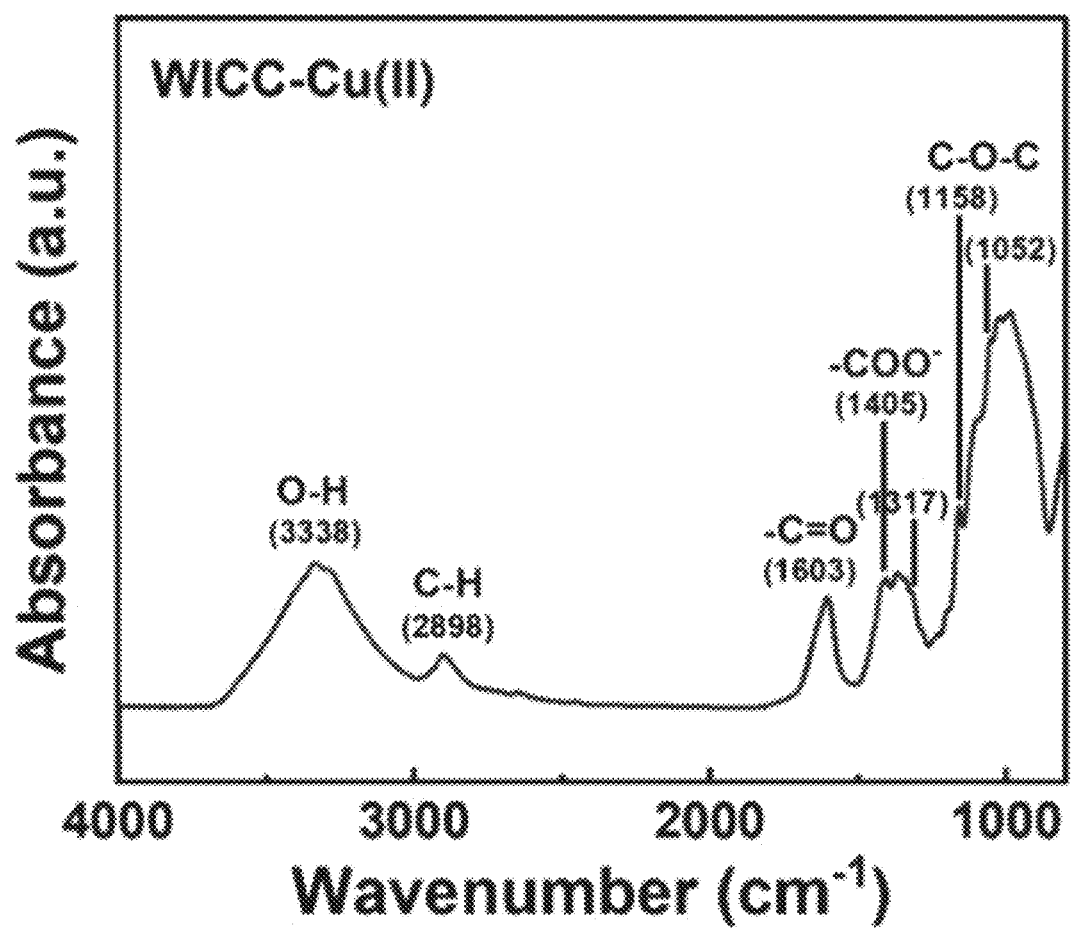
FIG. 7 shows the FTIR spectrum of the WICC-Cu(II) film.
Figure 8:
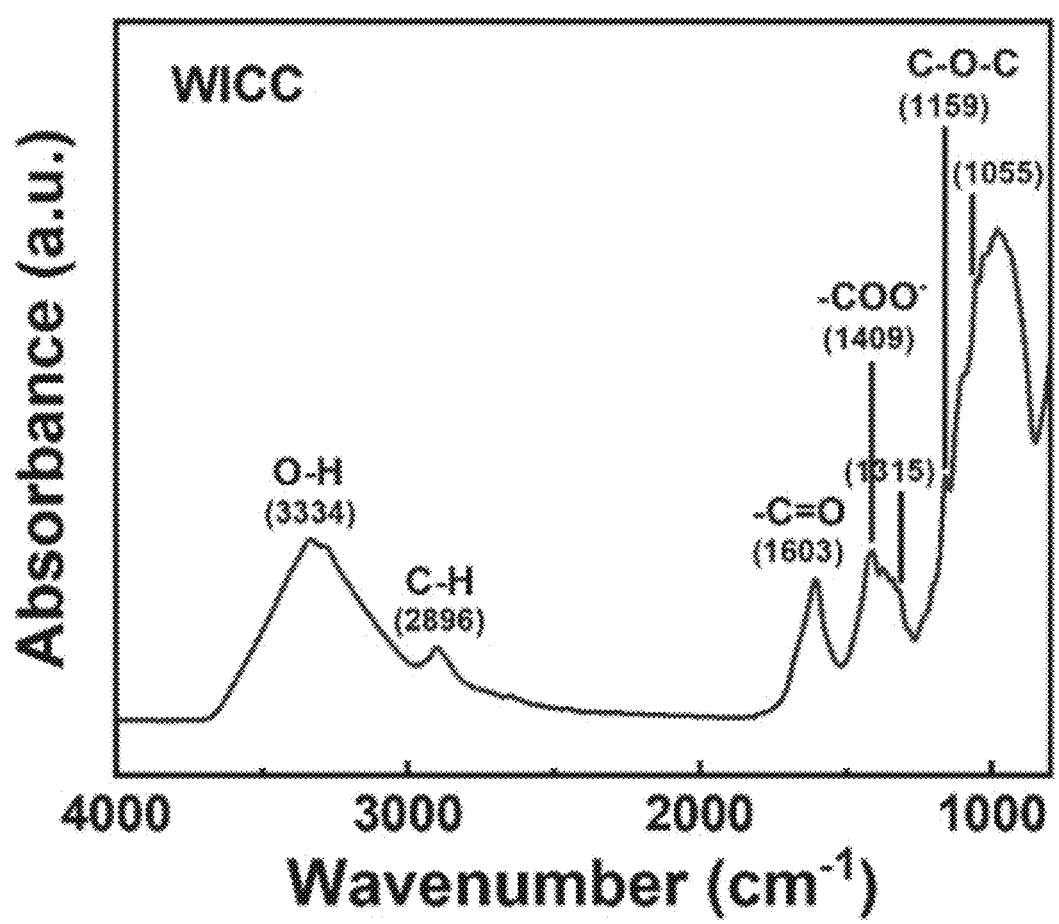
FIG. 8 shows the FTIR spectrum of the WICC film.

The inventor performs qualitative and quantitative analysis on the WICC film and WICC-0.50 mM Cu(II) films by using a Fourier infrared spectrum analyzer (Thermo Fisher, Inc, Nicolet 6700). FIG. 7 depicts the Fourier transform infrared (FTIR) spectrum of the WICC-0.50 mM Cu(II) film. The characteristic peaks of the WICC-0.50 mM Cu(II) film are quite similar to those of the WICC film, as depicted in FIG. 8, indicating that the introduction of $Cu^{2+}$ had no significant impact on the structure of WICC.

Figure 9:
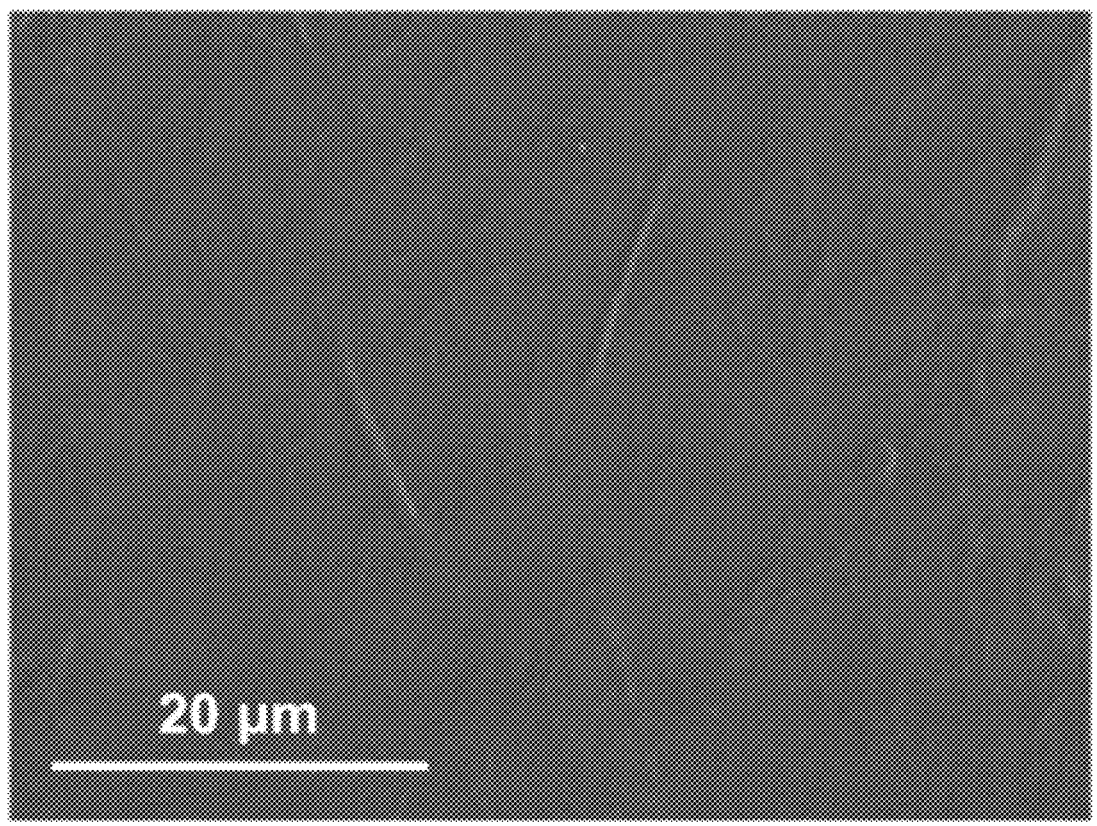
FIG. 9 shows the SEM image of the WICC-Cu(II) film.

Besides, the inventor performs scanning electron microscope on the WICC-0.50 mM Cu(II) film by using an electron scanning microscope (Hitachi limited corporation, S-3400N). The scanning electron microscopy (SEM) image of the WICC-0.50 mM Cu(II) film demonstrates its uniform surface, which also ensures the high transmittance of the film, as depicted in FIG. 9. Briefly, the WICC-0.50 mM Cu(II) film can be simply prepared through solution method without causing the aggregation of WICC or metal ions, which further guarantees the sensing performance and transmittance of WICC-0.50 mM Cu(II) sensors made from WICC-0.50 mM Cu(II) films.

Figure 10:
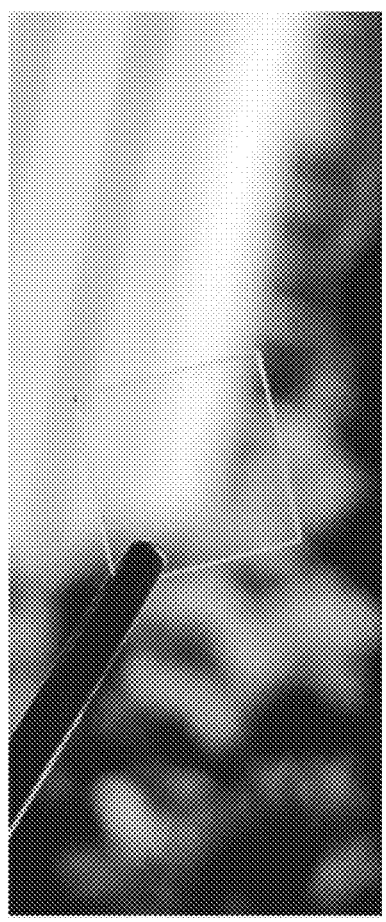
FIG. 10 shows the photo of the WICC-0.5 mM Cu(II) film deposited on quartz glass.

Then the inventor present a finished product of the WICC-0.50 mM Cu(II) film, which is shown by the photo of the WICC-0.5 mM Cu(II) film deposited on quartz glass, as depicted in FIG. 10.

The inventor multi-dimentionally explores the WICC-Cu (II) sensor on the flexibility, limit of detection, capacitance, impedance, normalized response and response time before and after exposed to MPEA.

The inventor measures the limit of detection and normalized response of the WICC-Cu(II) sensor and also performs bending test on the WICC-Cu(II) sensor, which are briefly explains the calculation and operation thereof.

Calculation of Normalized Response

For the standard deviation test, the devices are completely enclosed in a chamber and tested in the ambient atmosphere at about 75% relative humidity and room temperature. The LCR meter is used to collect the detection signals with a frequency of 400 Hz. Before testing, the devices remained stationary until the baseline stabilized. A certain amount of the MPEA is injected into the chamber using a syringe, which is rapidly evaporating into gas by heating. Upon contacting the MPEA, the devices exhibited a change in capacitance. After that, the MPEA gas in the chamber gradually diluted until it returned to the atmospheric environment before next testing. The obtained raw data are normalized and converted into normalized response using Formula 1:

$$\frac{\Delta C_P}{C_0} = \frac{C_0 - C_P}{C_0} \times 100\% \tag{1}$$

wherein $C_0$ and $C_P$ represent the capacitance values at the initial and measurement stages, respectively. $\Delta C_P$ serves as the changes of the capacitance values from $C_0$ to $C_P$.

Calculation of Limit of Detection

The limit of detection (LOD) is the lowest measured concentration that can be detected by a detection method (ISO 11843-1). Because the limit of detection (LOD) has a more precise definition and better generality, EP17-A2 *Guidelines for the Evaluation of Detection Limits and Limits of Quantification in Clinical Laboratories* recommends the use of LOD to express analytical sensitivity. It is used to define the measured presence or absence in the sample.

According to the regulation of IUPAC in 1975, the inventor defines that LOD, the signal produced by the WICC-Cu(II) sensor is represented as $x_L$, the average value of the blank signal is represented as $x_B$, and the standard deviation of the blank signal is represented as $s_B$. The calculation formula of LOD is as follows.

$$x_L = \bar{x}_B + k^* s_B$$

Wherein, k is a constant and is relevant to the choice of confidence level, $s_B = R^2$, R is root mean square deviation.

$$LOD = \frac{(x_L - \bar{x}_B)}{m}$$

Wherein, m is defined as the sensitivity of analysis and can be shown as the slop of the linear regression equation.

$$LOD = \frac{(k * R^2)}{m}$$

The inventor adopts k=3 and the allowed confidence level reaches 99.86%.

Operation of Bending Test

The bending test is treated with the FIB/SEM two-beam system in-situ three-point bending test by the FEI Quanta 200 3D focused particle beam/scanning electron microscopy system equipped with a gallium ion source and an Omni-Probe 100 micromanipulation probe from Oxford Instruments.

For the WICC-Cu(II) sensor used for the three-point bending test, the size standard refers to the sample size specification A in ASTM C1161-13, that is, 25 mm×2.0 mm×1.5 mm, which is reduced in equal proportion to the thickness of the WICC-Cu(II) sensor. It is 25 μm×2.0 μm×1.5 μm. In order to ensure that the fracture of the films can be observed in the bending experiment of the WICC-Cu(II) sensor, The thickness of the WICC-Cu(II) sensor as the three-point bending test sample is increased from 1.5 μm to 2 μm, that is, 25 μm×2.0 μm×2 μm. The bending test is tested at least 3 times for each sample (4 times for the multilayer film sample). According to the film three-point bending sample size, use FIB to cut on the WICC-Cu(II) sensor surface, and ensure that the dimensional accuracy is not less than ±0.05 μm.

According to ASTM C1161-13, the deformation rate in the test process should be in the order of $10^{-4} \cdot s^{-1}$, and the deformation rate can be shown in formula (1). Wherein, $\varepsilon_r$ is the deformation rate, d is the sample thickness, s is the indenter advance speed, and L is the width of the support beam (groove).

$$\varepsilon_r = \frac{6ds}{L^2} \tag{1}$$

Since the minimum step size of Omniprobe 100 is 100 nm, a compromise solution is adopted for in-situ bending test: move one step every 10 s, that is, 100 nm, and a deformation rate of $1.4 \times 10^{-4} \cdot s^{-1}$ can be obtained. Based on formula (1), at time t, the shape variable can be represented by formula (2). Where $\varepsilon$ is the shape variable at time t and is the distance that the indenter (here, the tip of the probe) moves.

$$\varepsilon = \frac{6dst}{L^2} = \frac{6dS}{L^2} \tag{2}$$

As a matter of fact, in order to map the capacitance linearly into a specific scope, i.e. [0, 1], the inventor adopts the normalization method to process capacitance data, which can be specified by the following formula.

$$x' = \frac{x - \min(x)}{\max(x) - \min(x)}$$

wherein, x is the tested capacitance in real time, x' is the normalized capacitance, max (x) is the maximum of the tested capacitance and min (x) is the minimum of the tested capacitance.

Now the wood-derived ionic conductive cellulose-Cu(II) sensor, i.e. WICC-Cu(II) sensor, for sensing N-methylphenethylamine, i.e. MPEA, is described in detail.

Figure 11:
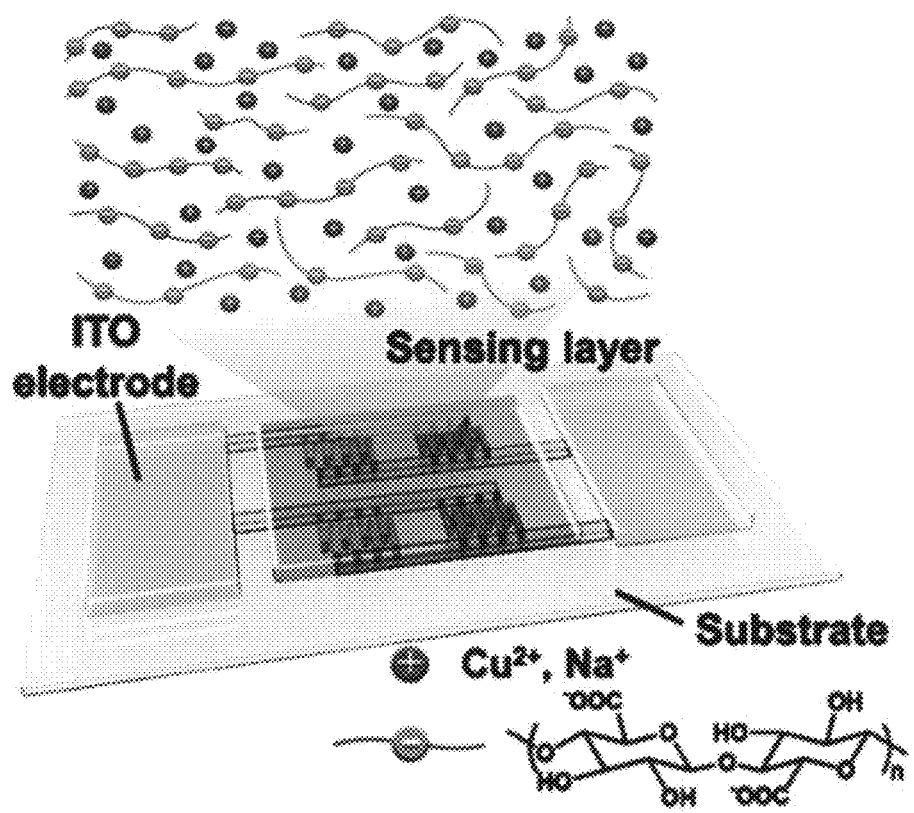
FIG. 11 shows the schematic diagram of the WICC-Cu(II) sensor.

As depicted in FIG. 11, the WICC-Cu(II) sensor comprises the above-mentioned WICC-Cu(II) film as the sensing layer, two transparent patterned electrodes as the cathode and the anode connecting the WICC-Cu(II) film; and a transparent substrate on which the two transparent patterned electrodes and the WICC-Cu(II) film are laid in sequence, wherein the patterned electrodes connect the two opposite sides of the sensing layer through their electric contact plates respectively and crosswisely. It should be noted that the substrate should be treated with plasma pretreatment before the WICC-Cu(II) film is coated on the substrate.

Seen from FIGS. 5 and 6, free metal ions, such as $Na^+$ and $Cu^{2+}$, are introduced in the WICC-Cu(II) film, which means the prepared WICC solution is rich with $Na^+$ due to the TEMPO treatment and the later addition of $Cu^{2+}$ can enhance the electroconductibility of the WICC-Cu(II) sensing layer, i.e. the WICC-Cu(II) film. Moreover, the shown electrode is a patterned electrode, i.e. indium tin oxide (ITO) functions as the highly transparent patterned electrodes, wherein the counter electrode is platinum sheet and the auxiliary electrode is a saturated calomel electrode, and quartz glass/polyethylene terephthalate (PET) act as rigid/flexible transparent substrates.

Figure 12:
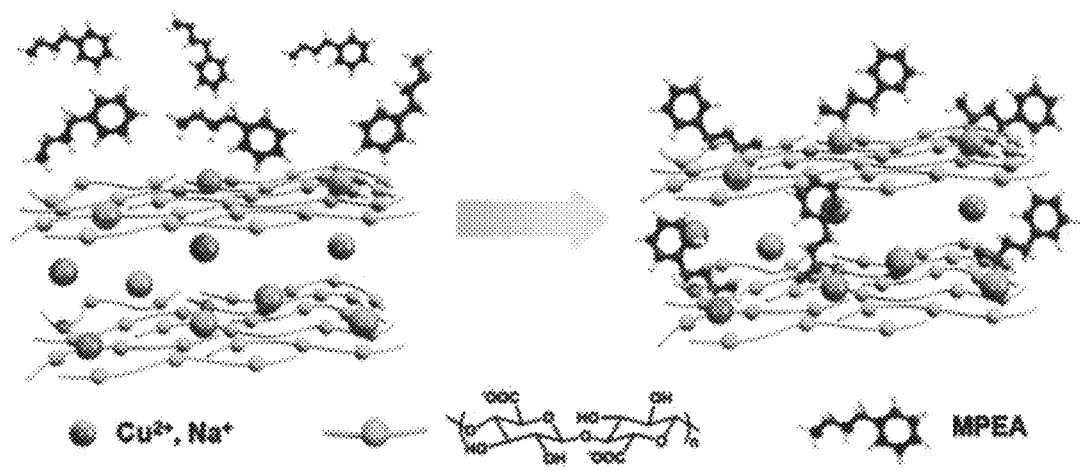
FIG. 12 shows the schematic diagram of sensing mechanism of the WICC-Cu(II) sensor to MPEA.

The inventor now proceeds to explain the above-mentioned WICC-Cu(II) sensor by firstly briefly depicting the sensing mechanism of the WICC-Cu(II) sensor to MPEA, as shown in FIG. 12. The sensing mechanism is that due to the ion conductivity characteristic of the WICC-Cu(II) film, the higher impedance means fewer mobile ions within the sensors. The metal ions in the sensing layer interaction with MPEA, which reduce the concentration of mobile ions, thereby leading to a decrease in the capacitance of the WICC-Cu(II) sensor.

Figure 13:
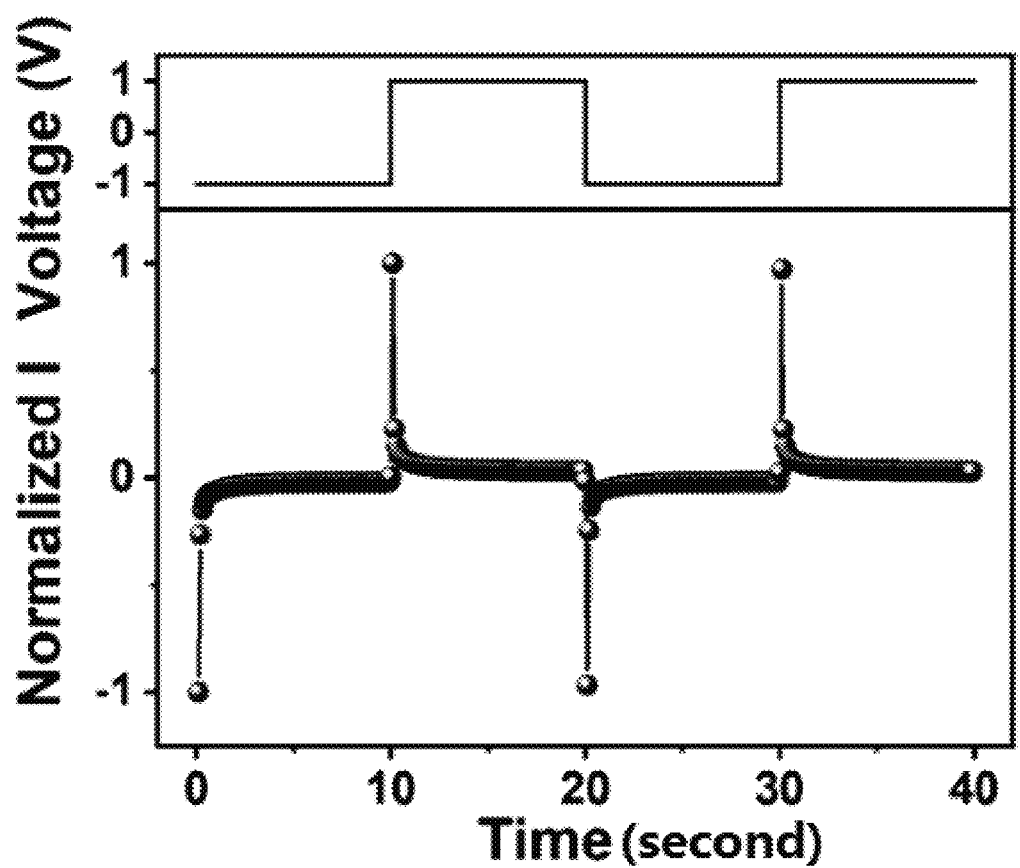
FIG. 13 shows the I-t curve of the WICC-Cu(II) sensor.

To validate the ion conductivity characteristic of the WICC-Cu(II) film, DC voltage sequences are employed to the sensors, as shown FIG. 13. When a positive voltage of 1 V is applied, the current of the devices decreased in a short period of time. Subsequently, when a negative voltage of –1 V is applied, the reverse current is also rapidly reduced. This phenomenon proves the ion conductivity property of the sensitive material.

Now the experiments where the response of the WICC-Cu(II) sensor on MPEA is introduced to further clarify the excellent selectivity and conductivity thereof.

Figure 14:
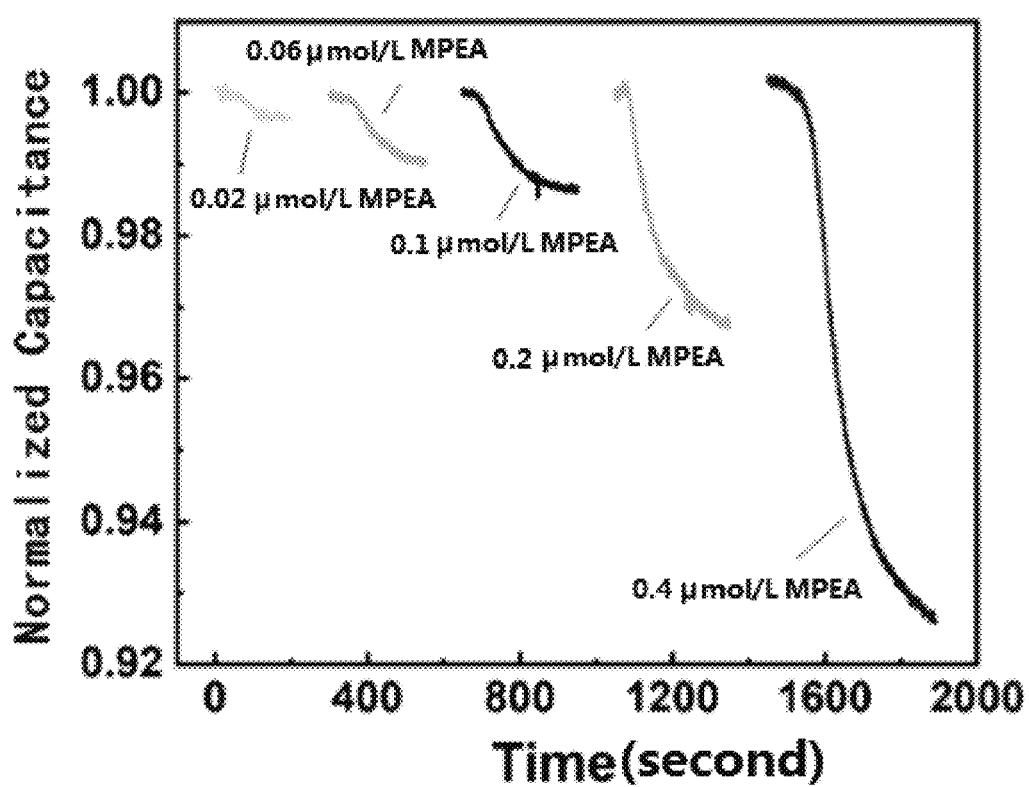
FIG. 14 shows the responses of the WICC-Cu(II) sensor to different concentrations of MPEA.

To evaluate the sensing performance of the WICC-Cu(II) sensors, the devices are enclosed in a chamber connected with a LCR meter to examine the responses to different concentrations of the detection target MPEA. As shown in FIG. 14, once exposed to specific concentrations of MPEA, the capacitance of the devices rapidly decreased, and then gradually reached a stable status. Besides, as the concentration of MPEA increased, the response of the devices to MPEA increased. The Normalized responses of the WICC-Cu(II) sensor exposed to different concentrations of MPEA are shown in Table 4.

TABLE 4

Normalized Responses of the WICC-Cu(II) Sensor Exposed to Different Concentrations of MPEA

| Concentrations of MPEA (μL) | 0.02 | 0.06 | 0.1 | 0.2 | 0.4 |
|---|---|---|---|---|---|
| Normalized response | 0.31% | 0.94% | 1.38% | 3.23% | 7.3% |

Notably, even when the devices are exposed to an extremely low concentration of MPEA, i.e. about 0.02 μL (1.7 ppm), an obvious response could still be observed. It can also be concluded from FIG. 14 that the WICC-Cu(II) sensor has a response about 0.31% when exposed to about 0.02 μL (1.7 ppm) MPEA.

Figure 15:
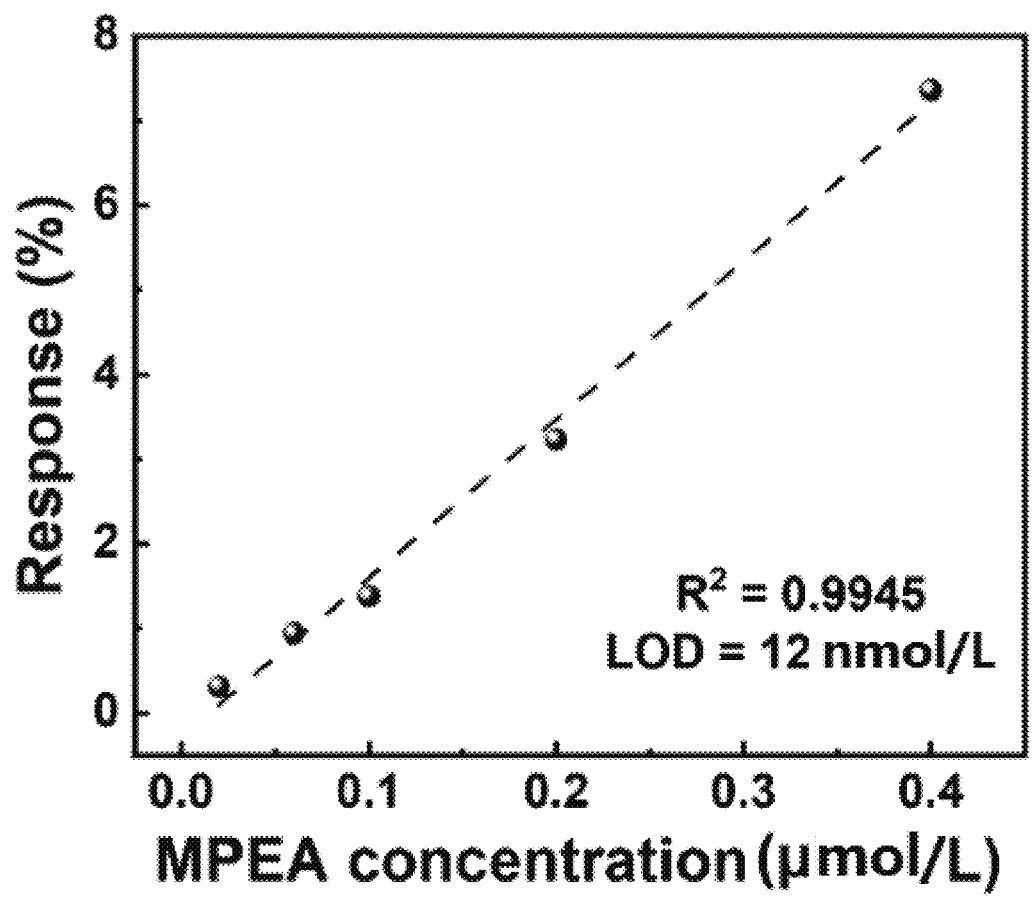
FIG. 15 shows the corresponding relationship between the responses and MPEA concentrations.

Considering the volatilization process of MPEA, the lower concentration of MPEA corresponds to the faster response time. Moreover, the response of the devices to MPEA is almost linearly correlated with MPEA concentration, as depicted in FIG. 15. As a result, the LOD is calculated to be about 12 nL (1 ppm), which demonstrated the high sensitivity and low detection limit of the WICC-Cu(II) sensors. It is noteworthy that after the devices are exposed to MPEA, the capacitance of the devices did not recover to the initial state, exhibiting the irreversible responses.

Figure 16:
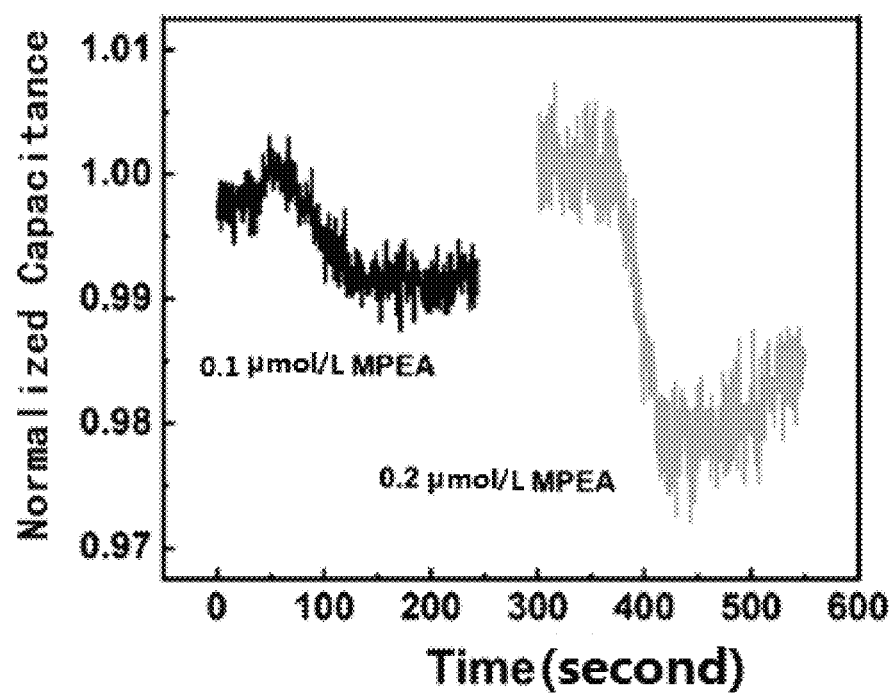
FIG. 16 shows the responses of the WICC sensor to different concentrations of MPEA.
Figure 17:
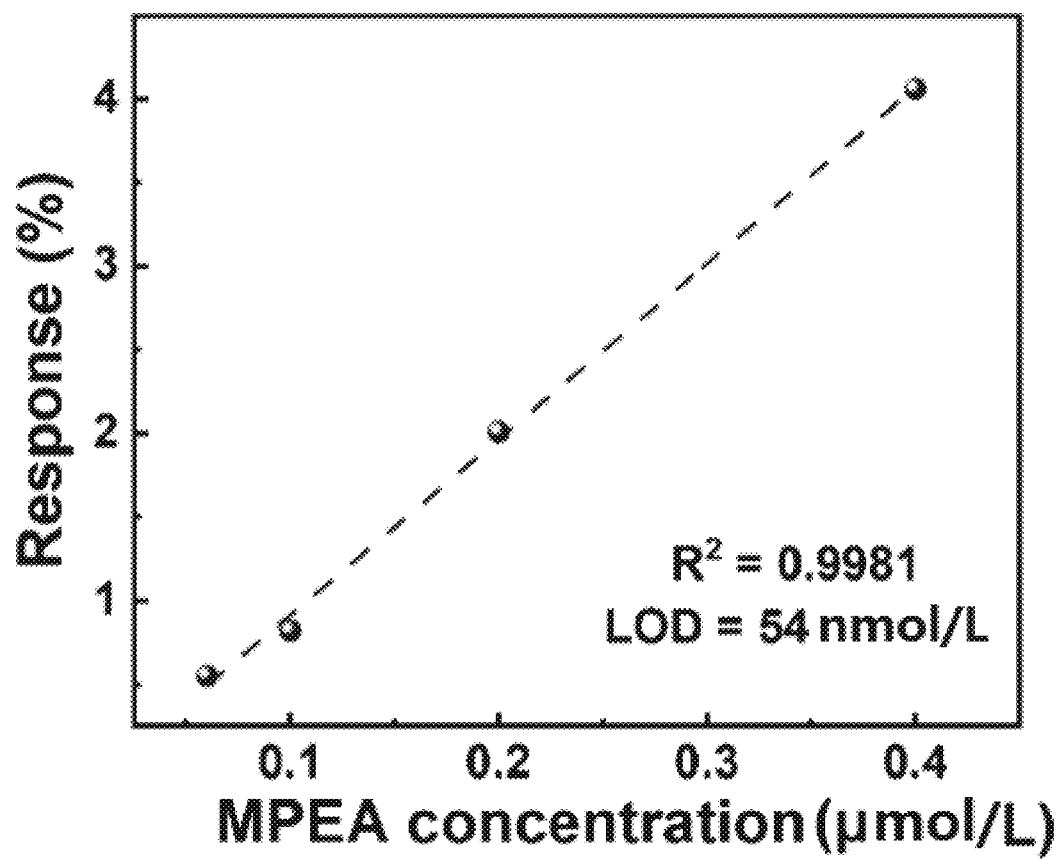
FIG. 17 shows the corresponding relationship between the responses and MPEA concentrations.

The inventor also repeats the above experimental and evaluation steps to a conventional WICC sensor, the results of which are shown in FIG. 16 and FIG. 17. The Normalized responses of the WICC sensor exposed to different concentrations of MPEA are shown in Table 5.

TABLE 5

Normalized Response of the WICC Sensor Exposed to Different Concentrations of MPEA

| Concentrations of MPEA (μL) | 0.1 | 0.2 |
|---|---|---|
| Normalized response | 0.82% | 2.0% |

It can be concluded that only when the devices are exposed to an extremely high concentration of MPEA, i.e. 0.1 μL (8.6 ppm), can an obvious response be observed. As a result, the LOD is calculated to be about 54 nL (4.6 ppm), which demonstrated the low sensitivity and high detection limit of the WICC sensors.

Figure 18:
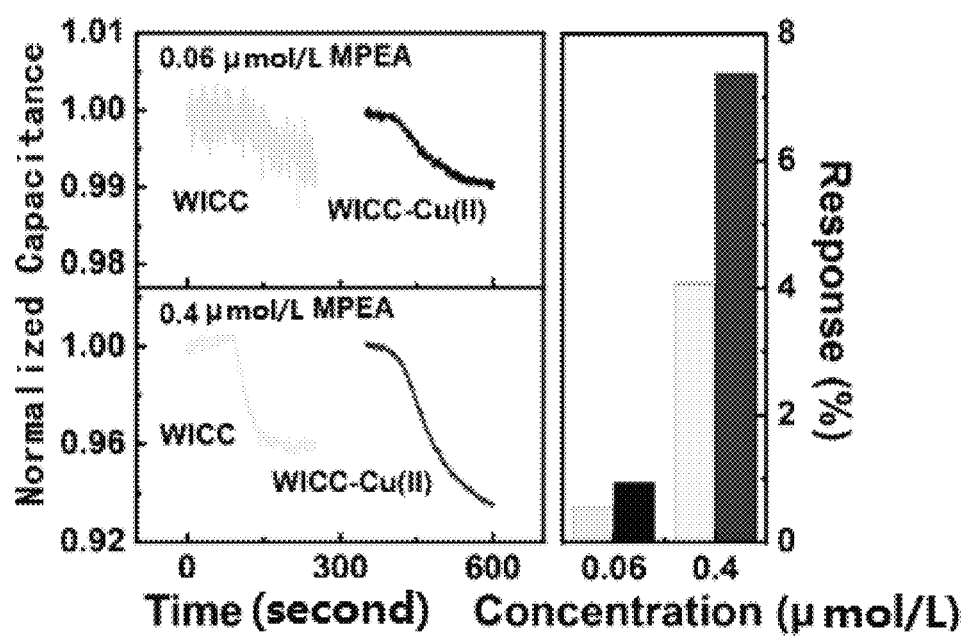
FIG. 18 shows the comparison of the responses of the WICC sensor and WICC-Cu(II) sensor to different concentrations of MPEA.

To prove the effect of the introduction of $Cu^{2+}$ in WICC on the detection capability, the responses of the WICC sensors to MPEA are investigated. The inventor observes the difference between the responses when the WICC-Cu(II) sensor exposed to different concentration of MPEA, whose results are shown in FIG. 18. Normalized responses of the WICC sensor and the WICC-Cu(II) sensor respectively to 0.06 μL (5.1 ppm) and 0.4 μL (34 ppm) of MPEA are shown in Table 6.

TABLE 6

Normalized Responses of the WICC Sensor and the WICC-Cu(II) Sensor Respectively to 0.06 μL and 0.4 μL of MPEA

| | WICC sensor | | WICC-Cu(II) sensor | |
|---|---|---|---|---|
| Concentration of MPEA (μL) | 0.06 | 0.4 | 0.06 | 0.4 |
| Normalized response | 0.55% | 4.1% | 0.94% | 7.3% |

As depicted in FIG. 17 and FIG. 18, it can be concluded that due to the volatilization function of MPEA, the lower the concentration of MPEA is, the shorter response time is the WICC-Cu(II) sensor. Moreover, the WICC sensors also exhibited irreversible responses to MPEA, and a relatively linear relationship between response and MPEA concentration is still obtained. However, compared to the WICC-Cu(II) sensors, the WICC sensors revealed smaller responses with larger noise. The decreased noise in the WICC-Cu(II)

sensors can be attributed to the introduction of $Cu^{2+}$, which raises the content of conductive ions in the sensing layer, and subsequently increases the basic capacitance of the devices. Furthermore, when exposed to 0.06 μL (5.1 ppm) MPEA, almost no apparent response is achieved in the WICC sensor, while an obvious response could still be obtained in the WICC-Cu(II) sensor. Besides, when the concentration of MPEA increased to 0.4 μL (34 ppm), the response of the WICC-Cu(II) sensor enhanced by 80% compared with that of the WICC sensor. Thus, the presence of $Cu^{2+}$ can not only improve the response of sensors but also decrease the detection limit to MPEA.

Figure 19:
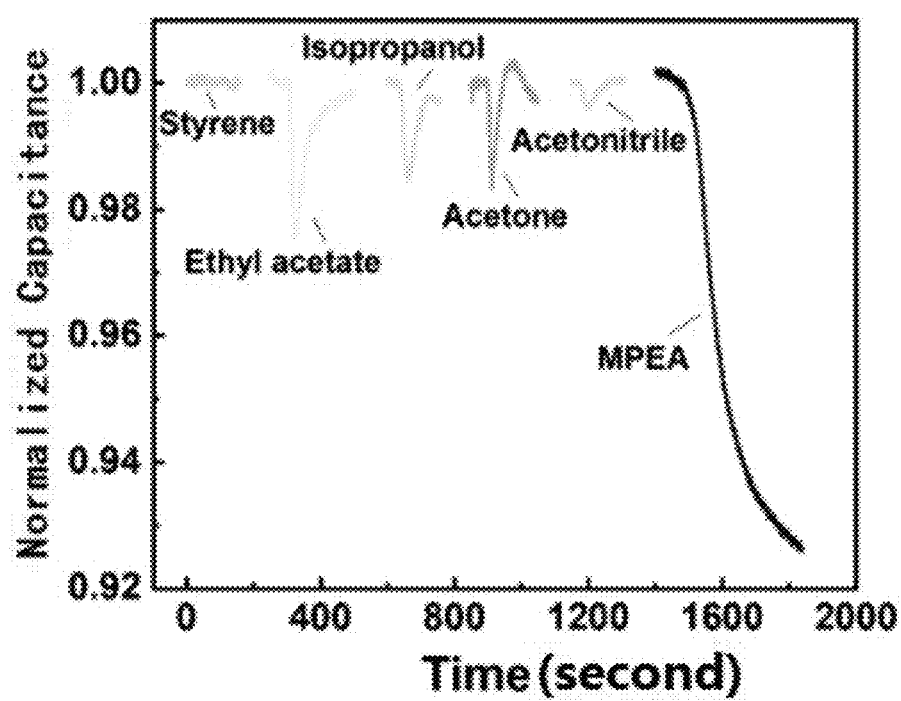
FIG. 19 shows the responses of the WICC-Cu(II) sensor to MPEA and interfering substances with the same concentration.

In order to evaluate the anti-interference capability of the WICC-Cu(II) sensors, different interfering substances (including styrene, ethyl acetate, isopropanol, acetone, and acetonitrile) with the same concentration are utilized. As depicted in FIG. 19, when exposed to the interfering substances, the capacitance of the devices rapidly decreased, and then nearly recovered to the initial state.

The inventor tests the short-term normalized response and the long-term normalized responses of WICC-Cu(II) sensor exposed to different substances at a concentration of 0.4 μL (34 ppm) and respective results are shown in Table 8 and Table 9.

TABLE 8

Short term-normalized Responses of the WICC-Cu(II) Sensor Exposed to Different Substances

| Substances | MPEA | styrene | ethyl acetate | isopropanol | acetone | acetonitrile |
|---|---|---|---|---|---|---|
| Short term-normalized Responses | 7.3% | 0.05% | 2.5% | 1.5% | 1.4% | 0.41% |

TABLE 9

Long-term normalized Responses of the WICC-Cu(II) Sensor Exposed to Different Substances

| Substances | MPEA | styrene | ethyl acetate | isopropanol | acetone | acetonitrile |
|---|---|---|---|---|---|---|
| Long-term normalized Responses | 7.4% | 0.05% | 0.20% | 0.23% | 0.29% | 0.10% |

Figure 20:
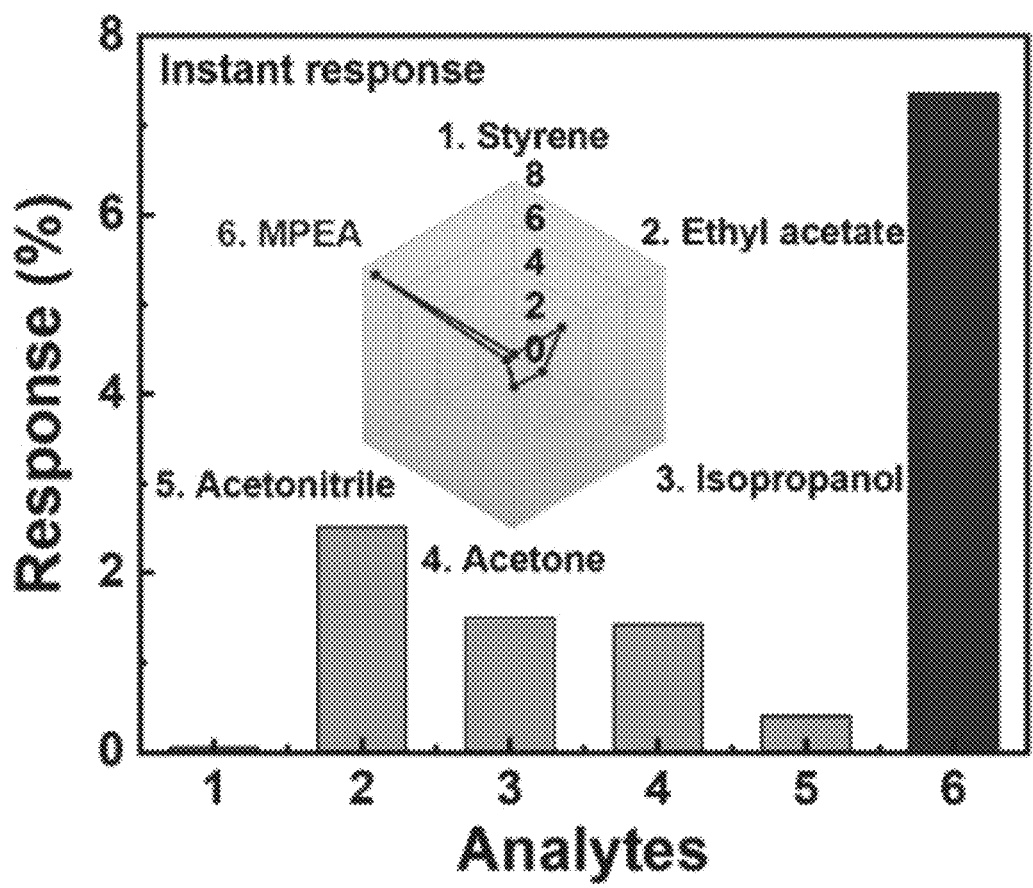
FIG. 20 shows the short term-normalized responses to MPEA and interfering substances.
Figure 21:
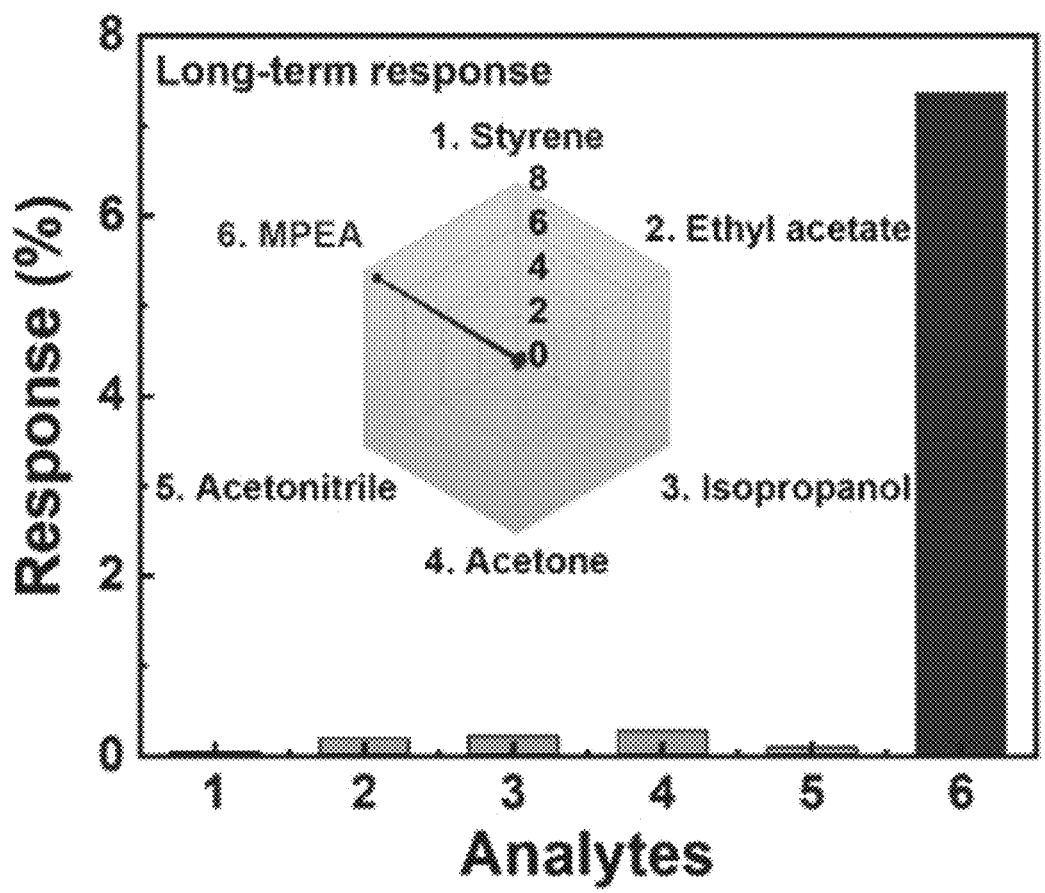
FIG. 21 shows the long-term normalized responses to MPEA and interfering substances.

For all the tested interfering substances, the devices exhibited small, short-term, and reversible responses, which are completely different from the responses to MPEA, as depicted in FIG. 20 and FIG. 21. Seen from the above table, the WICC-Cu(II) sensor has a short term-normalized response about 7.3% and a long term-normalized response about 7.4%, which are all much higher than those of the other interference substances.

The inventor then tests the short-term normalized response and the long-term normalized responses of 10 WICC-Cu(II) sensors exposed to MPEA at a concentration of 0.4 μL (34 ppm) and respective results are shown in Table 10 and Table 11.

TABLE 10

Short term-normalized Responses of the WICC-Cu(II) Sensor Exposed to MPEA of 0.4 μL (34 ppm)

| No. | 1 | 2 | 3 | 4 | 5 | 6 | 7 | 8 | 9 | 10 |
|---|---|---|---|---|---|---|---|---|---|---|
| Short term-normalized Responses | 7.2% | 7.3% | 7.2% | 7.5% | 7.8% | 7.6% | 7.4% | 7.3% | 7.6% | 7.7% |

TABLE 11

Long term-normalized Responses of the WICC-Cu(II) Sensor Exposed to MPEA of 0.4 μL (34 ppm)

| No. | 1 | 2 | 3 | 4 | 5 | 6 | 7 | 8 | 9 | 10 |
|---|---|---|---|---|---|---|---|---|---|---|
| Long term-normalized Responses | 7.5% | 7.8% | 7.6% | 7.4% | 7.9% | 8.1% | 7.8% | 7.6% | 7.9% | 7.7% |

It can be concluded from the above tables that WICC-Cu (II) sensor has a short term-normalized response in a range about 7.3%~7.8% and a long term-normalized response in a range about 7.4%~8.1% exposed to MPEA at a concentration of 0.4 µL (34 ppm).

The diverse responses to different substances suggest that the WICC-Cu(II) sensors have a weak interaction capability with the mentioned interfering substances but a strong interaction capability with MPEA, demonstrating the excellent anti-interference characteristic of the WICC-Cu(II) sensors. This further enables the WICC-Cu(II) sensors to well recognize the presence of MPEA even under complex detection conditions and demonstrates great potential for practical addictive drug detection.

The inventor also observes the difference of capacitance and impedance of the WICC-Cu(II) sensors before and after exposed to MPEA.

Figure 22:
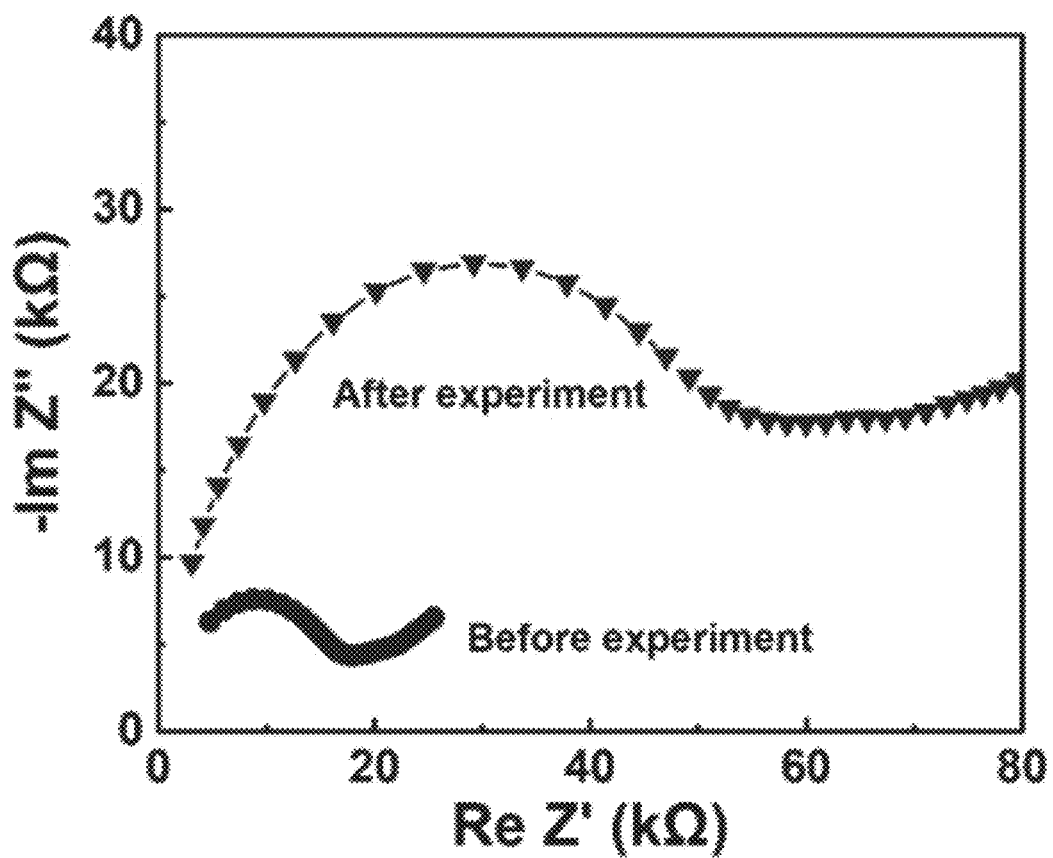
FIG. 22 shows the Nyquist plots of the WICC-Cu(II) film before and after exposed to MPEA.

The inventor uses the Nyquist plot to reflect the response property of the WICC-Cu(II) sensor under sinusoidal signal functions, whose result is shown in FIG. 22. The Nyquist plot indicates that the impedance of the WICC-Cu(II) sensors after the exposure of MPEA is higher than that before the exposure.

Figure 23:
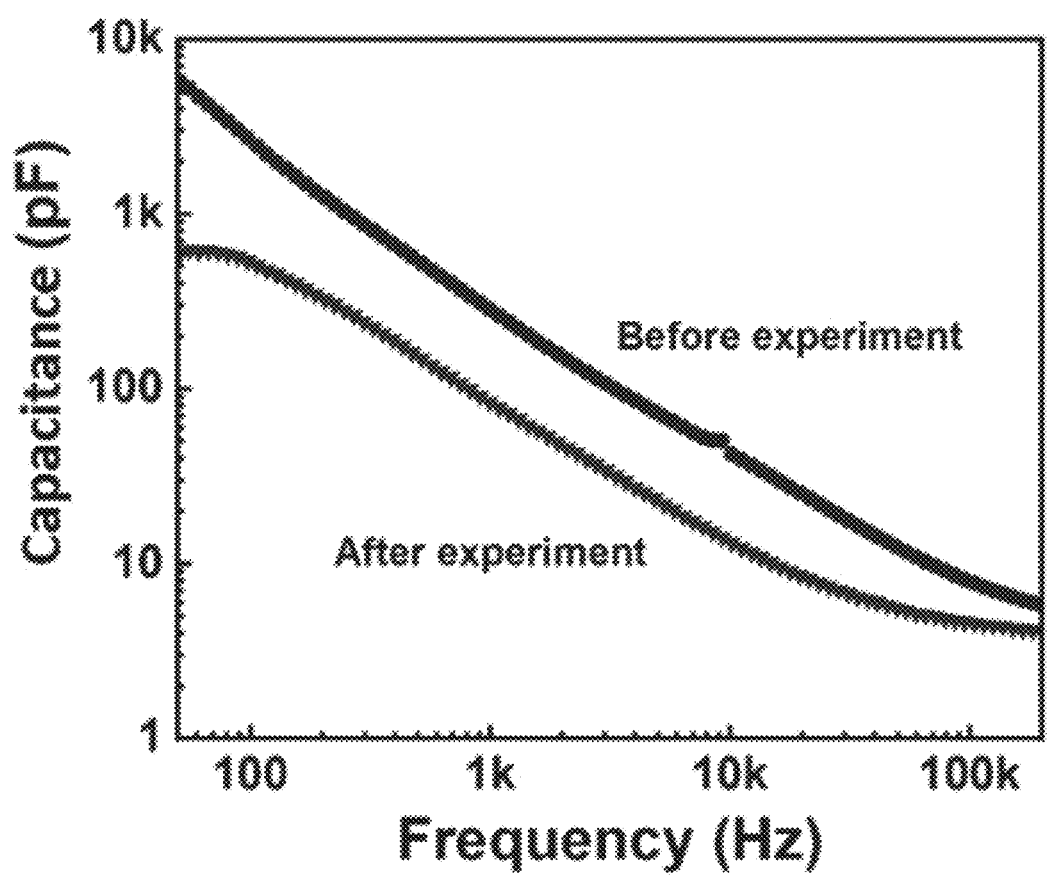
FIG. 23 shows the capacitance-frequency curve of the WICC-Cu(II) sensor before and after exposed to MPEA.

The inventor plots the capacitance-frequency curve for the WICC-Cu(II) sensors before and after exposed to MPEA, whose result is shown in FIG. 23. It can be concluded that, as the testing frequency increased, the capacitance of the devices before and after exposed to MPEA decreased. The WICC-Cu(II) sensor has an initial capacitance about 4.5-5.9 nF before exposed to MPEA and the WICC-Cu(II) sensor has a test capacitance about 0.54-0.63 nF after exposed to MPEA. These results reveal that the WICC-Cu(II) sensors own a high initial capacitance and can be operated within a wide frequency range.

The inventor continues to explore the flexibility of the WICC-Cu(II) film by performing bending tests thereon.

Figure 24:
FIG. 24 shows the photo of the flexible WICC-Cu(II) sensor.

Befitting from the intrinsic flexibility of the WICC-Cu(II) film, a flexible WICC-Cu(II) sensor is fabricated based on the PET substrate with patterned ITO electrodes. As depicted in FIG. 24, the flexible WICC-Cu(II) sensor still exhibited high transmittance. The inventor calculates the normalized response after bending different cycles, whose result are shown in Table 12 and Table 13 and depicted in FIGS. 25 and 26.

TABLE 12

Response Times of the WICC-Cu(II) Sensor Before and After Bending

|  | Before bending | After bending |
| --- | --- | --- |
| Response time (seconds) | 0-90 | 100-210 |

TABLE 13

Normalized Responses of the WICC-Cu(II) Sensor After Bending Different Cycles

| Bending cycles | 0 | 200 | 500 | 1000 |
| --- | --- | --- | --- | --- |
| Normalized response | 1.40% | 1.27 % | 1.18% | 1.16% |

Figure 25:
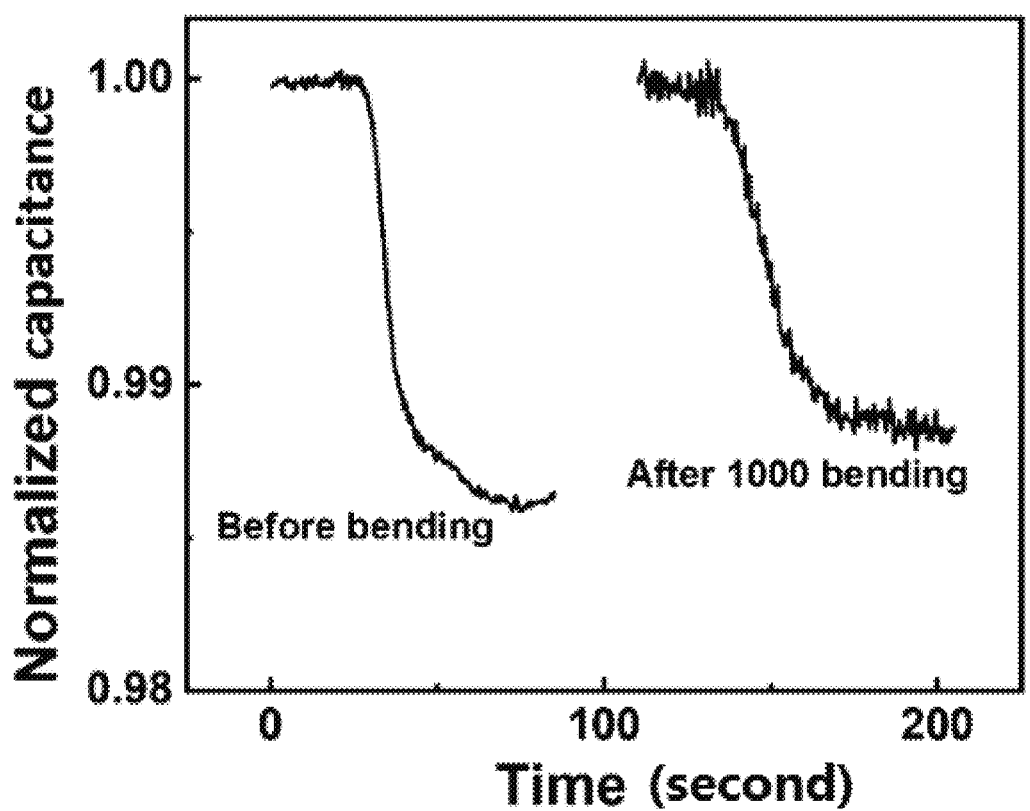
FIG. 25 shows the responses of the flexible WICC-Cu(II) sensor to MPEA before and after 1000 bending cycles.
Figure 26:
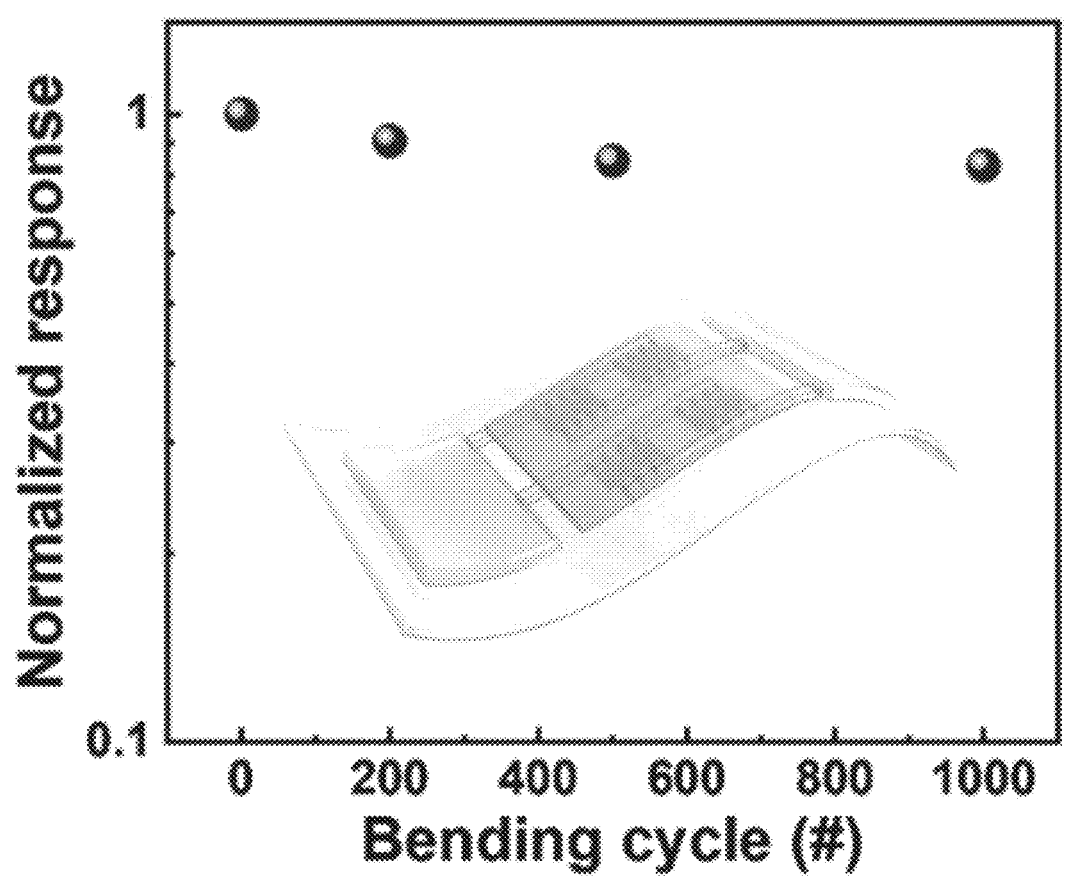
FIG. 26 shows the comparison of the responses of the flexible WICC-Cu(II) sensor to MPEA before and after different bending cycles.

As depicted in FIG. 25 and FIG. 26, the response of the flexible sensors to the same concentration of MPEA before bending (1.40%) is almost identical to that of the rigid sensors (1.38%). After undergoing a series of bending times, no significant response attenuation is observed, indicating the outstanding flexibility of the WICC-Cu(II) sensors.

Figure 27:
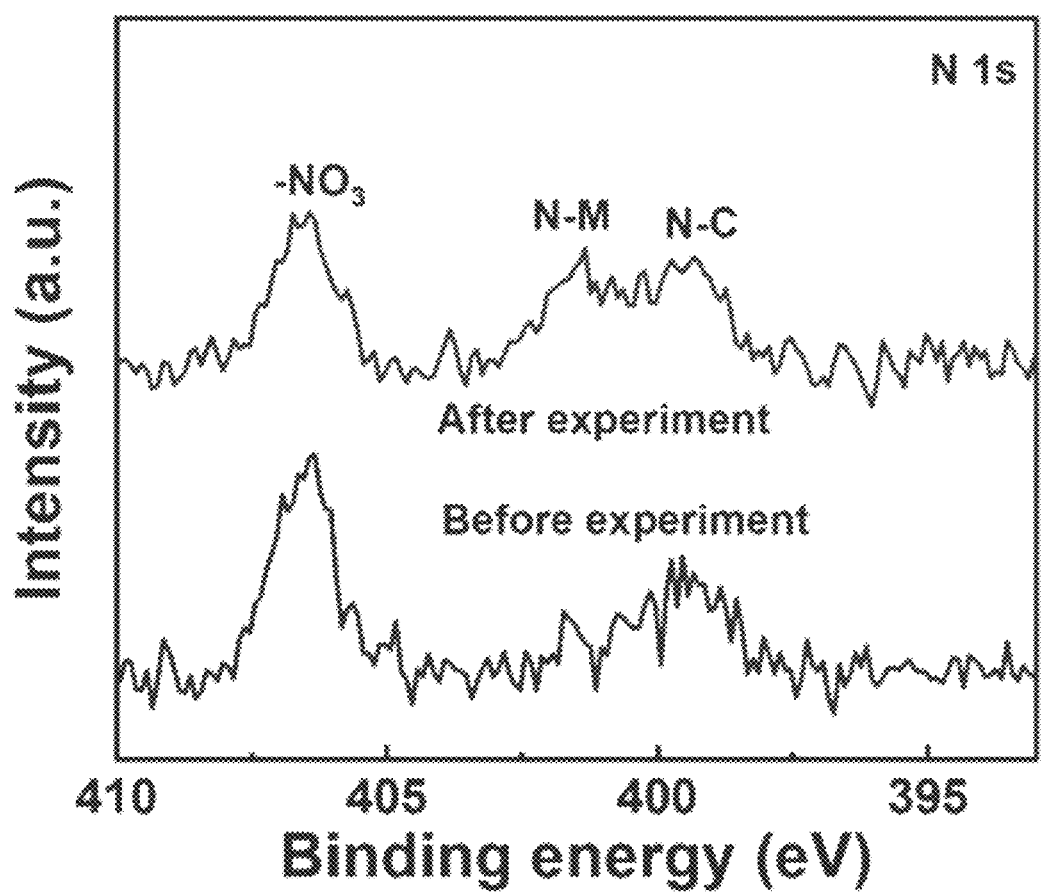
FIG. 27 shows N 1s spectra of the WICC-Cu(II) film before and after exposed to MPEA.
Figure 28:
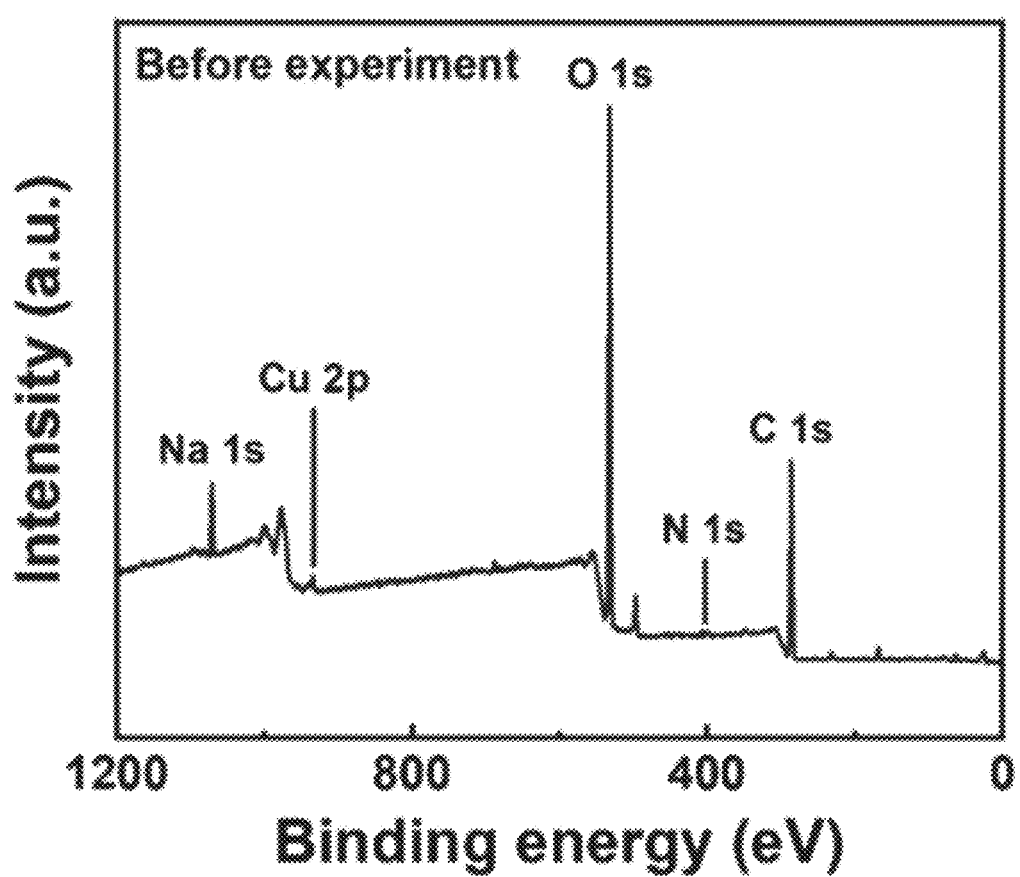
FIG. 28 shows the XPS spectra of the WICC-Cu(II) film before exposed to MPEA.
Figure 29:
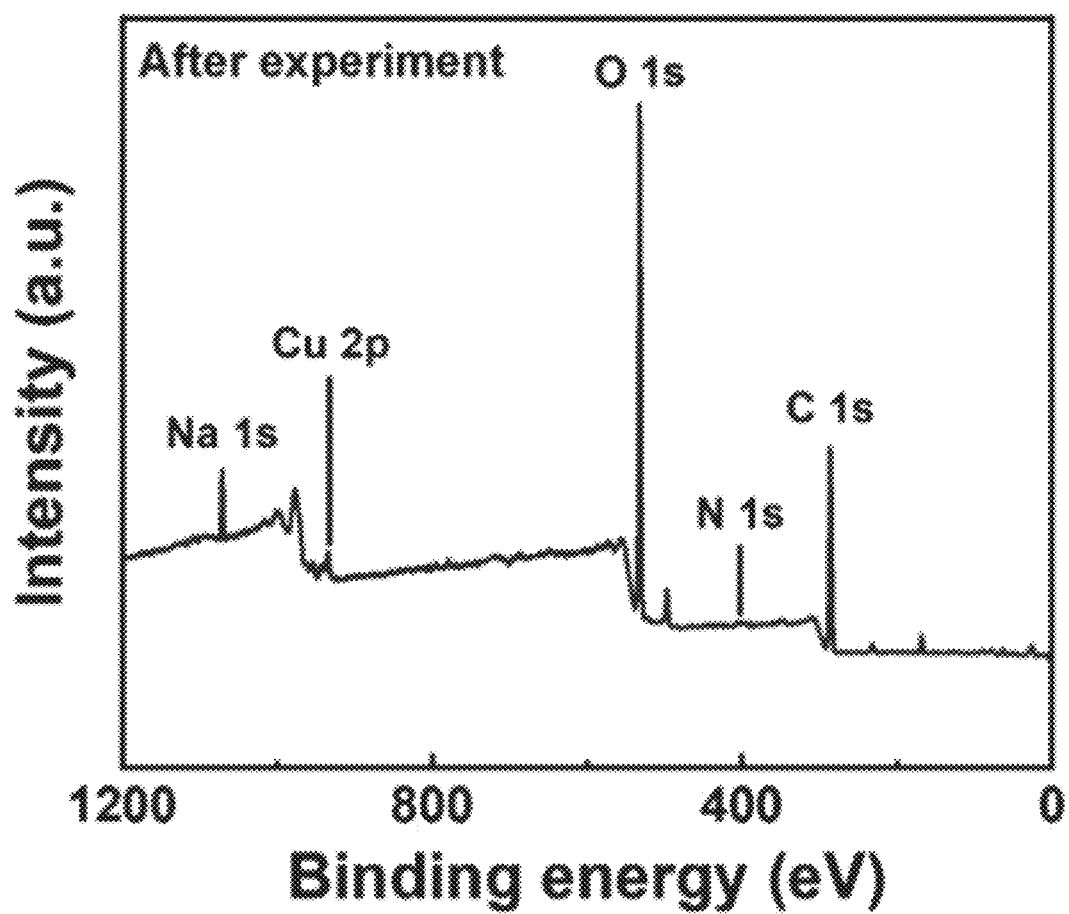
FIG. 29 shows the XPS spectra of the WICC-Cu(II) film after exposed to MPEA.
Figure 30:
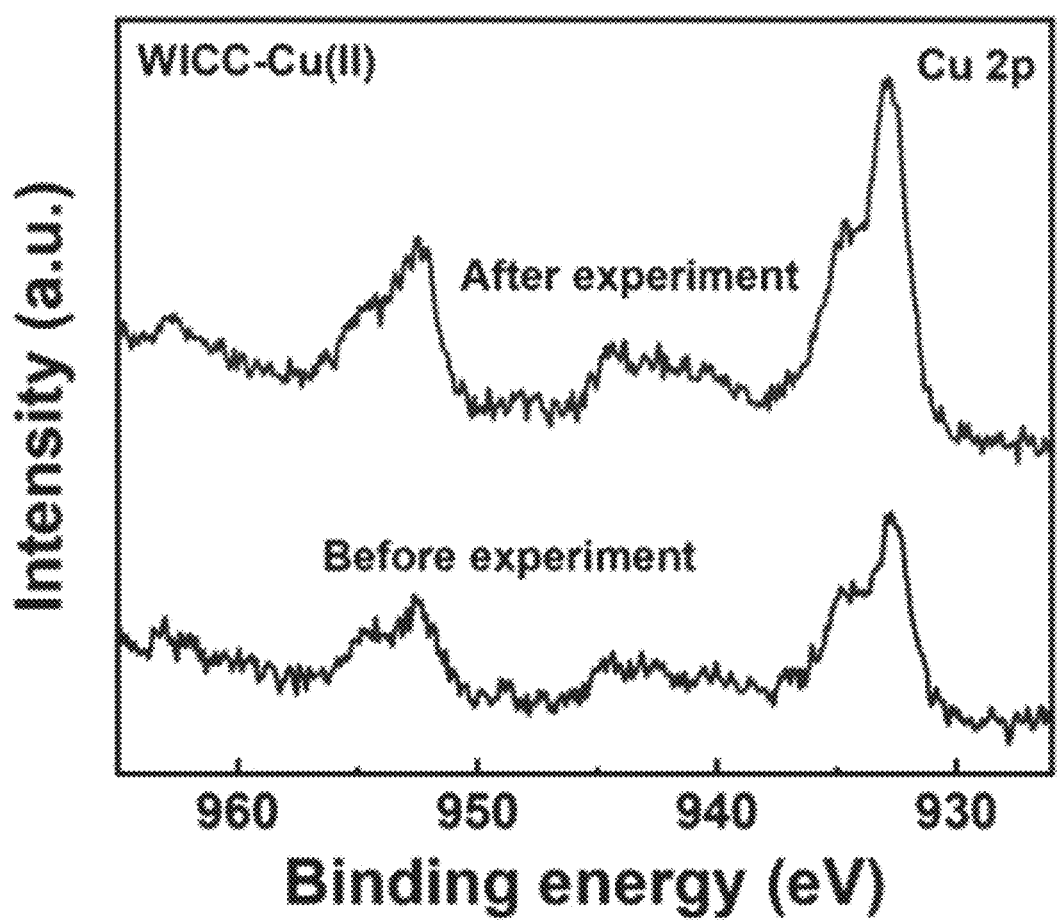
FIG. 30 shows the Cu 2p spectra of the WICC-Cu(II) film before and after exposed to MPEA.
Figure 31:
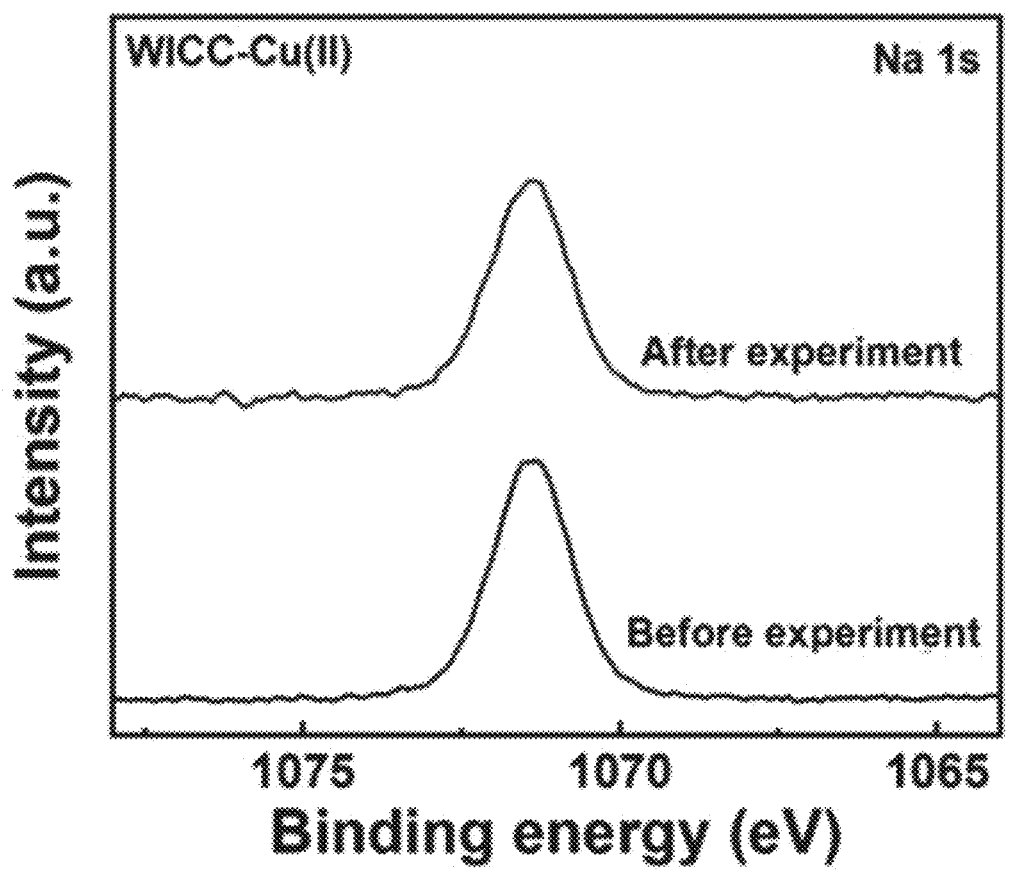
FIG. 31 shows the Na 1s spectra of the WICC-Cu(II) film before and after exposed to MPEA.

In order to further reveal the sensing mechanism of the WICC-Cu(II) sensor, XPS is further employed. As depicted in FIG. 27, —$NO_3$ came from the introduction of nitrate ions caused by the $Cu(NO_3)_2$ solution. After exposed to MPEA, a new peak corresponding to N-metal ions (N-M) is observed, which could be attributed to the interaction of the metal ions (M=$Cu^{2+}$, $Na^+$) present in the WICC-Cu(II) layer with MPEA. The formation of N-M structure explains the irreversible responses of the devices to MPEA. In contrast, due to the absence of N-M structure formation, the above interfering substances may not stably interaction with the sensing layer, resulting in small and reversible responses. In addition to the N 1s spectra of the WICC-Cu(II) film, no significant variation is observed in the Cu 2p spectra and Na 1s spectra before and after the exposure of MPEA, as depicted in FIGS. 28-31.

In summary, the inventor has demonstrated transparent and flexible sensors based on WICC-Cu(II) as the ionic conductive material for detecting MPEA. Befitting from the exceptional ion conductivity, the WICC-Cu(II) sensors exhibited excellent selectivity, ultralow LOD (about 12 nL, 1 ppm), and flexibility performance. The achievement of flexible WICC-Cu(II) sensors suggests a new avenue for the development of transparent chemical sensors for detecting addictive drug.

Befitting from irreversible and specific responses of the WICC-Cu(II) sensors to MPEA, the sensors demonstrated high selectivity. Furthermore, the sensors exhibited other outstanding detection capabilities for MPEA at room temperature, including low detection volume (0.02 µL, 1.7 ppm) and an ultralow theoretical detection limit (LOD, 12 nL, 1 ppm). More significantly, the flexible WICC-Cu(II) sensors could maintain detection performance comparable to the initial state even after 1000 bending tests, which would facilitate their integration into various portable and wearable electronics. The proposed transparent and flexible sensors based on green WICC material provide a new approach to developing invisible chemical sensors for the detection of addictive drugs.

All publications and patent applications cited in the specification are herein incorporated by reference in their entirety. It will be apparent to those of ordinary skill in the art that certain changes and modifications may be made thereto without departing from the spirit or scope of the appended claims.

What is claimed is:

1. A method of preparing a wood-derived ionic conductive cellulose-Cu(II) film (WICC-Cu(II) film), wherein the WICC-Cu(II) film has a transmittance over 87% despite the introduction of $Cu^{2+}$, wherein the method comprises:
    (1) preparing softwood pulp suspension in a concentration of 0.08 g/mL, (2,2,6,6-tetramethylpiperidin-1-yl)-oxidanyl homogeneous solution in a concentration of 1 g/mL (TEMPO homogeneous solution), sodium bromide homogeneous solution in a concentration of 0.01 g/mL (NaBr homogeneous solution) and copper nitrate trihydrate solution in a concentration of 100 mM (Cu $(NO_3)_2$ solution);
    (2) mixing the NaBr homogeneous solution with the TEMPO homogeneous solution to prepare NaBr/TEMPO blended solution, then adding the NaBr/TEMPO blended solution and sodium hypochlorite solution (NaClO solution), into the softwood pulp suspension to prepare a blended suspension;
    (3) maintaining the blended suspension at pH 8.8-10.5 for 3-5 hours to obtain a purified cellulose suspension, following by washing and diluting the purified cellulose suspension, which is then dispersed into nanofiber to obtain nanocellulose suspension;

(4) separating the nanofiber and the microfiber and collecting the supernatant to obtain a wood-derived ionic conductive cellulose homogeneous solution (WICC homogeneous solution);

(5) evenly mixing the WICC homogeneous solution with the $Cu(NO_3)_2$ solution and deionized water and then drop-coating the obtained solution onto a substrate whose surface is treated with plasma pretreatment and exposing the substrate at room temperature to cure the WICC-Cu(II) film for 10-13 hours, wherein the $Cu^{2+}$ concentration in the obtained solution is adjusted to about 0.5 mM.

2. A wood-derived ionic conductive cellulose-Cu(II) sensor (WICC-Cu(II) sensor), for sensing N-methylphenethylamine (MPEA), comprising:

a wood-derived ionic conductive cellulose-Cu(II) film (WICC-Cu(II) film) as a sensing layer, wherein the WICC-Cu(II) film has a transmittance over 87% despite the introduction of $Cu^{2+}$;

two transparent patterned electrodes as a cathode and an anode connecting the WICC-Cu(II) film; and a transparent substrate on which the two transparent patterned electrodes and the WICC-Cu(II) film are laid in sequence.

3. The WICC-Cu(II) sensor for sensing N-methylphenethylamine according to claim 2, wherein the lowest detection limit of the MPEA by the WICC-Cu(II) sensor is about 0.02 µL (1.7 ppm).

4. The WICC-Cu(II) sensor for sensing N-methylphenethylamine according to claim 2, wherein the theoretical detection limit of the WICC-Cu(II) sensor is about 12 nL (1 ppm).

5. The WICC-Cu(II) sensor for sensing N-methylphenethylamine according to claim 2, wherein the WICC-Cu(II) sensor has an initial capacitance of 4.5-5.9 nF before exposed to MPEA when tested at a frequency of 50 Hz.

6. The WICC-Cu(II) sensor for sensing N-methylphenethylamine according to claim 2, wherein the WICC-Cu(II) sensor has a test capacitance of 0.54-0.63 nF after exposed to MPEA when tested at a frequency of 50 Hz.

7. The WICC-Cu(II) sensor for sensing N-methylphenethylamine according to claim 2, wherein the WICC-Cu(II) sensor has a short term-normalized response in range about 7.3%-7.8% and a long-term normalized response in range about 7.4%-8.1% when exposed to 0.4 µL (34 ppm) of MPEA.

* * * * *